(12) United States Patent
Kiely et al.

(10) Patent No.: US 11,400,123 B2
(45) Date of Patent: Aug. 2, 2022

(54) COMBINATION PRODUCT FOR PROPHYLAXIS AND TREATMENT OF IRRITABLE BOWEL SYNDROME

(71) Applicant: PRECISIONBIOTICS GROUP LIMITED, Cork (IE)

(72) Inventors: Barry Kiely, County Cork (IE); Eileen Frances Murphy, Cork (IE); David Groeger, Cork (IE)

(73) Assignee: PrecisionBiotics Group Limited, Cork (IE)

( * ) Notice: Subject to any disclaimer, the term of this patent is extended or adjusted under 35 U.S.C. 154(b) by 0 days.

(21) Appl. No.: 16/767,846

(22) PCT Filed: Jan. 29, 2019

(86) PCT No.: PCT/EP2019/052134
§ 371 (c)(1),
(2) Date: May 28, 2020

(87) PCT Pub. No.: WO2019/145570
PCT Pub. Date: Aug. 1, 2019

(65) Prior Publication Data
US 2020/0289587 A1    Sep. 17, 2020

(30) Foreign Application Priority Data

Jan. 29, 2018  (EP) ................................. 18153992
Aug. 23, 2018  (EP) ................................. 18190595
Aug. 23, 2018  (EP) ................................. 18190598

(51) Int. Cl.
| | | |
|---|---|---|
| A61K 35/745 | (2015.01) | |
| A61P 1/00 | (2006.01) | |
| A23L 33/135 | (2016.01) | |
| A23C 9/123 | (2006.01) | |
| A61K 35/747 | (2015.01) | |
| A61K 9/19 | (2006.01) | |
| A61K 9/20 | (2006.01) | |
| A61K 9/48 | (2006.01) | |
| A61K 45/06 | (2006.01) | |

(52) U.S. Cl.
CPC .......... *A61K 35/745* (2013.01); *A23C 9/1234* (2013.01); *A23L 33/135* (2016.08); *A61K 35/747* (2013.01); *A61P 1/00* (2018.01); *A23Y 2220/00* (2013.01); *A23Y 2300/55* (2013.01); *A61K 9/19* (2013.01); *A61K 9/20* (2013.01); *A61K 9/48* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,195,906 B2* | 3/2007 | Collins | A61P 37/00 435/252.1 |
| 8,926,952 B2* | 1/2015 | Trejo | A61K 8/99 424/70.1 |
| 10,144,978 B2 | 12/2018 | O'Mahony et al. | |
| 2015/0209392 A1 | 7/2015 | Song et al. | |
| 2018/0282825 A1 | 10/2018 | O'Mahony et al. | |
| 2020/0289586 A1 | 9/2020 | Kiely et al. | |

FOREIGN PATENT DOCUMENTS

| | | |
|---|---|---|
| EP | 1743633 A1 | 1/2007 |
| EP | 2438821 A1 | 4/2012 |
| JP | 2007169200 A | 5/2007 |
| JP | 2017081853 A | 5/2017 |
| WO | WO 2010/055499 A2 | 5/2010 |
| WO | WO 2010/055499 A3 | 5/2010 |
| WO | WO 2010/060722 A1 | 6/2010 |
| WO | WO 2011/058535 A1 | 5/2011 |
| WO | WO 2013/074531 A1 | 5/2013 |
| WO | WO 2015/146844 A1 | 1/2015 |
| WO | WO 2018/002238 A1 | 1/2018 |
| WO | WO 2018/002240 A1 | 1/2018 |

OTHER PUBLICATIONS

Bravo, Javier A. et al., "Ingestion of Lactobacillus Strain Regulates Emotional Behavior and Central GABA Receptor Expression in a Mouse via the Vagus Nerve", *PNAS*, vol. 108, No. 38, pp. 16050-16055, (2011).

Herman, F.R., "The Effectiveness of Adding Pharmacologic Treatment With Clonazepam or Cyclobenzaprine to Patient Education and Self-Care for the Treatment of Jaw Pain Upon Awakening: A Randomized Clinical Trial", *Journal Orofac Pain*, 16(1) pp. 64-70, Winter (2002).

Mariesse, J. et al., "Lactobacillus Reuteri DSM 17938 and Bifidobacterium Longum Atcc BAA-999 Normalize Sleep Patterns in Prenatal Stress Rats", *Human Physiology and Pharmacology, University of Rome*, p. 797 (2011).

(Continued)

*Primary Examiner* — Vera Afremova
(74) *Attorney, Agent, or Firm* — Bookoff McAndrews, PLLC

(57) ABSTRACT

A combination product comprising an isolated strain of *Bifidobacterium* NCIMB 41003 and another strain which does not adversely interact with *Bifidobacterium* NCIMB 41003 improves gastrointestinal symptoms associated with IBS and improves one or more of mood, stress, anxiety, sleep quality and depression associated with IBS.

18 Claims, 19 Drawing Sheets

(56) References Cited

OTHER PUBLICATIONS

O'Manony,L. et al., "Probiotic Human Bifidobacteria: Selection of a New Strain and Evaluation In Vitro and In Vivo", *Gastroenterology*, & 55th *Annual Meeting of the Society-for-Surgery-of-the-Alimentary-Tract* (SSAT)/Digestive Disease We, vol. 118, No. 4, pp. AGAA774, (2000).
U.S. Appl. No. 16/9,768, filed Feb. 13, 2020.
Allen, A.P. et al., "Bifidobacterium Longum 1714 As A Translational Psychobiotic: Modulation Of Stress, Electrophysiology And Neurocognition In Healthy Volunteers", *Translational Psychiatry*, 6, e939 (2016).
Allen, A.P. et al., "Bifidobacterium Longum 1714: A Psychobiotic That Modulates Brian Activity, The Stress Response And Neurocognitive Performance In Healthy Volunteers", (2015).
Bravo, Javier A. et al., "Ingestion Of *Lactobacillus* Strain Regulates Emotional Behavior And Central GABA Receptor Expression In A Mouse Via The Vagus Nerve", *PNAS*, vol. 108, No. 38, pp. 16050-055, (2011).
Brenner, Darren M. et al., "The Utility Of Probiotics In The Treatment Of Irritable Bowel Syndrome: A Systematic Review", *The American Journal of Gastroenterology*, vol. 104, No. 4, pp. 1033-1049, (2009).
Buysse, Daniel J., et al., "Quantification Of Subjective Sleep Quality in Healthy Elderly Men And Women Using The Pittsburgh Sleep Quality Index (PSQI)", *Sleep*, 14 (4): pp. 331-338, (1991).
Buysse, Daniel J., et al., "The Pittsburgh Sleep Quality Index: A New Instrument For Psychiatric Practice And Research", *Psychiatry Research*, 28, pp. 193-213, (1988).
Colten, Harvey R., et al., "Sleep Disorders And Sleep Deprivation: An Unmet Public Health Problem", *The National Academies Press*, (2006).
Dinan, Timothy G., et al., "Psychobiotics: A Novel Class Of Psychotropic", *Science Diet*, Biological Psychiatry, vol. 74, Issue 10, pp. 720-726, (2013).
Fillingim, Roger B., et al., "Potential Psychosocial Risk Factors For Chronic TMD: Descriptive Data And Empirically Identified Domains From The OPPERA Case-Control Study", *Journal Pain*, (2012).
Herman, C.R., et al., "The Effectiveness Of Adding Pharmacologic Treatment With Clonazepam Or Cyclobenzaprine To Patient Education And Seif-Care For The Treatment Of Jaw Pain Upon Awakening: A Randomized Clinical Trial", *Journal Orofac Pain*, 16(1) pp. 64-70, Winter (2002).

Health and Nutritional Properties of Probiotics In *Food Including Powder Milk With Live Lactic Acid Bacteria*, (2001).
International Search Report for PCT/EP2019/052134 dated Apr. 17, 2019 (3 pages).
Jay, et al., "Modern Food Microbiology", 7th edition, (2005).
Kazemi, A. et al., "Effect Of Probiotic And PreBiotic vs Placebo On Psychological Outcomes In Patients With Major Depressive Disorder: A Randomized Clinical Trial", *Clinical Nutrition*, (2018), https://doi.Org/10.1016/j.clnu.2018.04.010.
Kell, Douglas B. et al., "Viability And Activity in Readily Culturable Bacteria: A Review And Discussion of The Practical Issues", https://link.springer.com/article/10.1023/A:1000664013047. (1998).
Mairesse, J. et al., "Lactobacillus Reuteri DSM 17938 And Bifidobacterium Longum Atcc BAA-999 Normalize Sleep Patterns In Prenatal Stress Rats", *Human Physiology And Pharmacology, University of Rome*, p. 797 (2011).
O'Mahony,L. et al., "Probiotic Human Bifidobacteria: Selection Of A New Strain And Evaluation In Vitro And In Vivo", *Gastroenterology*, & 55th *Annual Meeting Of The Society-For-Surgery-Of-The-Alimentary-Tract* (SSAT)/Digestive Disease We, vol. 118, No. 4, pp. AGAA774, (2000).
Pinto-Sanchez, Maria Ines et al., "Probiotic Bifidobacterium Longum NCC3001 Reduces Depression Scores And Alters Brain Activity: A Pilot Study In Patients With Irritable Bowel Syndrome", *Gastroenterology*, (2017).
Porto, Felipe et al., "Differences In Psychosocial Functioning And Sleep Quality Between Idiopathic Continuous Orofacial Neuropathic Pain Patients And Chronic Masticatory Muscle Pain Patients", *Journal of Orofacial Pain*, vol. 25 Issue 2, pp. 117-124 (2011).
Savignac, H.M. et al., "Bifidobacteria Exert Strain-Specific Effects On Stress-Related Behavior And Physiology In BALB/c Mice", *Neurogastroenterology & Motility*, 26, pp. 1615-1627 (2014).
Savignac, H.M. et al., Bifidobacteria Modulate Cognitive Processes In An Anxious Mouse Strain, *Behavioural Brain Research*, 287, pp. 59-72 (2015).
U.S. Appl. No. 16/789,768, filed Feb. 13, 2020.
Wang, "Effects Of Probiotics On Central Nervous System Functions In Humans", pp. 1-152 (2017).
Whorwell, Peter J., "Therapeutic Advances In Gastroenterolgy Review Do Probiotics Improve Symptoms In Patients With Irritable Bowel Syndrome?", Retrieved from the Internet: URL:https://journals.sagpub.com/doi/pdf/1 , (2009).

* cited by examiner

Open labelled study with COMBO with 'COMBO' for 8-weeks, followed by an 8-week washout 'COMBO' product: *B. longum* 35624 + *B. longum* 1714

(e)

(a)

(b)

Weak correlation (a)

No correlation (b)

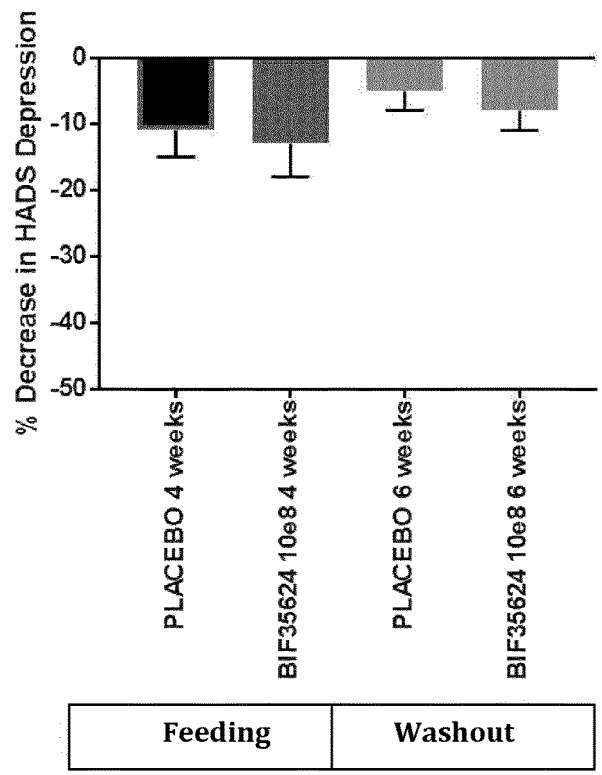
Fig. 8(a)
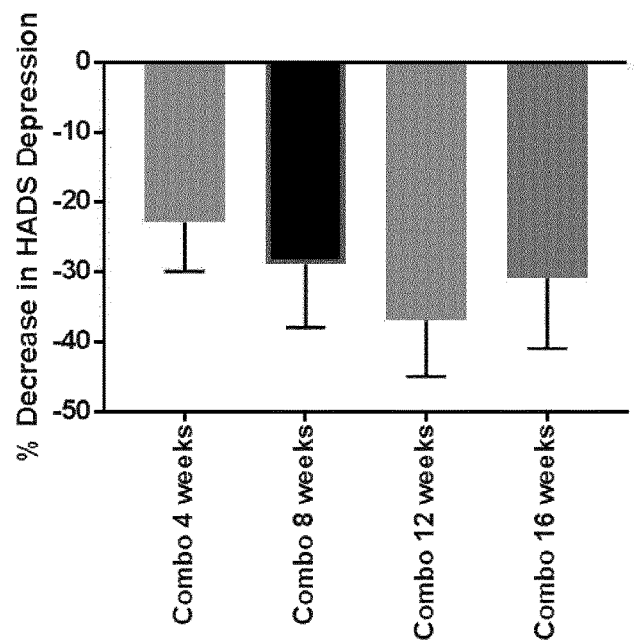
Fig. 8(b)
(% decrease from baseline)
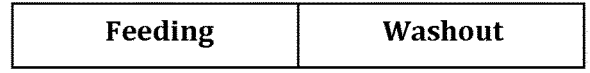

(a)

(b)

Minimum Score = 0 (better); Maximum Score = 21 (worse)

Q6 During the past month, how would you rate your sleep quality overall:

| Sleep Quality | Week 0 | Week 4 | Week 8 | Week 12 | Week 16 |
|---|---|---|---|---|---|
| Very bad | 3% | 3% | 5% | 8% | 3% |
| Fairly bad | 38% | 28% | 28% | 30% | 28% |
| Fairly good | 48% | 48% | 48% | 53% | 53% |
| Very good | 8% | 25% | 25% | 18% | 20% |

N=40

| Sleep Quality | Week 0 | Week 4 | Week 8 | Week 12 | Week 16 |
|---|---|---|---|---|---|
| Very bad | 17% | 6% | 6% | 11% | 0% |
| Fairly bad | 83% | 50% | 39% | 50% | 50% |
| Fairly good | 0% | 33% | 50% | 50% | 50% |
| Very good | 0% | 11% | 6% | 0% | 0% |

N=18

PSQI over 5

- AH1714/35624-Rif (2% each)
- Control (2% AH1714)
- Control (2% 35624-Rif)

- DPC6315/35624-Rif (2% each)
- Control (2% DPC6315)
- Control (2% 35624-Rif)

Dose of bacterial strains (a)

(b)

COMBINATION PRODUCT FOR PROPHYLAXIS AND TREATMENT OF IRRITABLE BOWEL SYNDROME

CROSS-REFERENCE TO RELATED APPLICATIONS

This application is the U.S. national phase entry under 35 U.S.C. § 371 of International Application No. PCT/EP2019/052134, filed on Jan. 29, 2019, which claims benefit of priority to European Application No. 18153992.5, filed on Jan. 29, 2018, and to European Application Nos. 18190595.1 and 18190598.5, each of which was filed on Aug. 23, 2018.

Irritable bowel syndrome (IBS) is characterized by chronic abdominal pain, discomfort, bloating, and alteration of bowel habits and affects 10-15% of the general population (Hungin et al., 2003). For many, this condition can be a debilitating. The underlying factors contributing to IBS are heterogeneous and not completely understood but it is considered that altered gut mucosal immune activation (O'Malley, 2015), cognitive function (Kennedy et al., 2014), psychological stress, brain-gut interaction and as well as changes in the gut microbiota are significant contributors to the condition (Drossman and Hasler, 2016).

The gastrointestinal tract contains a vast array of microorganisms (approximately 95% of all the cells in the human body are intestinal bacteria) that are very important to human health by providing protection against intestinal infections, supplying additional nutritional value from food by fermentation and contributing to the development of the immune system. Accumulating evidence suggests that IBS patients have different gut microbiota composition compared to healthy controls (Jeffery et al., 2012, Tap et al., 2017), and this altered microbiota can also be changed by psychological stress (Blanchard et al., 2008, Chitkara et al., 2008). Indeed, the gut microbiota has received attention as a possible core player in the development and persistence of IBS as it interacts with the gut-brain axis.

Probiotic bacteria are microorganisms believed to provide health benefits when consumed, and defined as "live microorganisms which, when administered in adequate amounts, confer a health benefit on the host" (FAO/WHO, 2001). Recent studies have shown promising effects of probiotics on the gut-brain axis in both preclinical and clinical studies (Dinan and Cryan, 2017).

For IBS, certain probiotic strains have been shown to reduce some or all of the gastrointestinal symptoms of irritable bowel syndrome (Ford et al., 2014, O'Mahony et al., 2005, Whorwell et al., 2006). The 35624 strain is the only probiotic that has been shown to affect the cardinal gut symptoms associated with IBS (Whorwell et al., 2006). However, little has been done to address the co-morbid symptoms of stress, anxiety and depression and little is known about the effects of probiotics on the gut-brain axis in IBS and there is no probiotic strain or combination of strains available that has demonstrated management of both the gastrointestinal symptoms and associated stress, anxiety and depression symptoms of IBS.

STATEMENTS OF INVENTION

According to the invention there is provided a formulation comprising an isolated strain of *Bifidobacterium* strain NCIMB 41003 and a second bacterial strain wherein the second strain does not adversely impact the gastrointestinal effects of strain NCIMB 41003.

The second strain may be a *Bifidobacterium* strain that does not adversely impact the gastrointestinal effects of strain NCIMB 41003.

The second strain may be a *Lactobacillus* strain that does not adversely impact the gastrointestinal effects of strain NCIMB 41003.

The second strain may be a *Lactococcus* strain that does not adversely impact the gastrointestinal effects of strain NCIMB 41003.

The second strain in some cases may be a *Bifidobacterium longum*, *Bifidobacterium bifidum*, *Bifidobacterium lactis*, *Bifidobacterium breve*, *Lactobacillus acidophilus*, *Lactobacillus brevis*, *Lactobacillus casei*, *Lactobacillus salivarius* *Lactococcus lactis*, *Lactobacillus acidophilus*, or *Lactobacillus rhamnosus* that does not adversely impact the gastrointestinal effects of strain NCIMB 41003.

The following strains are available from Danisco *B. lactis* HN019, *L. acidophilus* NCFM (ATCC PTA-4797), *L. rhamnosus* HN001, *B. lactis* Bi-07, *B. lactis* B420, *B. lactis* B1-04.

The additional strain may be one or more of the strains included in a multispecies probiotic composition available from Winclove which comprises one or more viable *Lactobacillus* strains chosen from the group consisting of *B. Bifidum* W23, *B. lactis* W51, *B. lactis* W52, *Lactobacillus acidophilus* W37, *Lactobacillus, brevis* W63, *Lactobacillus casei* W56, *Lactobacillus casei* W56, *Lactobaillis salivarius* W24, *Lactococcus lactis* W19, *Lactococcus lactis* W58.

In some embodiments the second strain:
improves mood associated with IBS;
reduces stress associated with IBS;
reduces anxiety associated with IBS;
improves sleep quality associated with IBS;
treats depression associated with IBS; and/or
normalises dysregulated cortisol awakening response associated with IBS The formulation may contain more than one additional strain.

According to the invention there is provided a combination product comprising an isolated strain of *Bifidobacterium* strain NCIMB 41003 and a second *Bifidobacterium* strain for use in the prophylaxis or treatment of irritable bowel syndrome (IBS) by improving gastrointestinal symptoms associated with IBS and one or more of the following:
improving mood associated with IBS;
reducing stress associated with IBS;
reducing anxiety associated with IBS;
improving sleep quality associated with IBS;
treating depression associated with IBS; and
normalising dysregulated cortisol awakening response associated with IBS.

The combination product may comprise an isolated strain of *Bifidobacterium* strain NCIMB 41003 and a second *Bifidobacterium* strain for use in the prophylaxis or treatment of irritable bowel syndrome (IBS) by improving gastrointestinal symptoms associated with IBS and normalising dysregulated cortisol awakening response associated with IBS.

The second strain in some cases is not *B. longum* 1714® (NCIMB 41676). As an alternative to *B. longum* 1714® another *B. longum* strain which is compatible with *B. longum* 35624® and provides one or more of the properties of the 35624/1714 may also be utilised. Potential examples include:
*Bifidobacterium longum* R175 ("Rosen® 175"), is marketed by Lallemand (France) under the reference probiocap Rosell ME-175.

*B. longum* NCC3001 (ATCC BAA-999) from Nestle is a synonym of *B. longum* BB536 available from Morinaga Milk Industry Co., Ltd.

The second *Bifidobacterium* strain should not adversely impact the gastrointestinal effects of strain NCIMB 41003. This may be determined by suitable in vitro and/or in vivo testing such as outlined in examples 6 and 7 herein.

We have surprisingly found that a combination product incorporating bacterial strains *B. longum* 35624® (NCIMB 41003) and *B. longum* 1714™ (NCIMB 41676) leads to a surprising, sustained, positive effect even after feeding stops.

We have surprisingly found that a combination product incorporating bacterial strains *B. longum* 35624® (NCIMB 41003) and *B. longum* 1714™ (NCIMB 41676) leads to a surprising, sustained, positive effect even after feeding stops.

IBS has many elements involved in its pathophysiology. Both gastrointestinal and depressive/anxious symptoms are co-morbid along with an underlying low-grade inflammation which is known to effect both symptoms (Enck et al. 2016). Looking to address all these elements would beneficially address all aspects of IBS as no prior art adequately addresses these other co-morbidities fully.

Creating a combination product containing the 35624 strain is not straightforward. 35624 is a sensitive strain and does not grow easily with or tolerate the presence of other strains. The cytokine profile of 15 different B. longums was assessed in a PBMC assay including 1714™ strain and DPC6315 (example 6). 1714 and DPC6315 strains were chosen for further work as DPC6315 had the highest IL-10/IL-12 anti-inflammatory ratio and changes in mood including depression and anxiety can be linked to inflammation.

1714 had demonstrated an anti-inflammatory cytokine profile in vitro and positive effects on mood in both animal and human trials.

35624 was shown to tolerate both 1714 and DPC6315 in growth experiments (example 5).

When the combination of 35624 and 1714 was consumed by a human IBS cohort there was a surprising effect as not only did the combination address IBS gastrointestinal symptoms, it also addressed the gut-brain aspects of IBS, and new synergistic effects were seen that were unexpected (examples 1-4). IBS symptoms improved and the dysregulated Cortisol Awakening Response (CAR) was normalised during the feeding period but these effects were lost post feeding. Surprisingly, persistence of an anti-anxiolytic effect and improvement in depression, sleep quality, as well as a reduction in the pro-inflammatory cytokine TNF-α was observed even after feeding had stopped. Post-feeding persistence of reductions in TNF-α (improved anti-inflammatory tone) has not been observed when feeding with 35624 strain alone (FIG. 11).

We further assessed the combination of *B. longum* DPC6315 and 35624 in vitro (example 6). This combination maintains its high IL-10 signal, similarly to 35624 and 1714. We investigated the combination of DPC6315 and 35624 in a well-established animal model normally used for screening anti-inflammatory substances (example 7). No synergistic effects were seen with the combination and very unexpectedly the presence of 6315 cancelled out the effect of 35624 and the combination was worse than the single strain 35624 alone. Therefore, it is not obvious that every combination of *B. longum* strains will work together even from established in vitro immune profiles tests and it would not therefore have been possible to predict the outcome of the 35624/1714 combination trial in advance.

Also provided is a formulation comprising an isolated strain of *Bifidobacterium* NCIMB 41003 and an isolated strain of a second *Bifidobacterium* strain that does not adversely impact the gastrointestinal effects of strain NCIMB 41003.

The invention also provides a formulation comprising an isolated strain of *Bifidobacterium* NCIMB 41676 and an isolated strain of *Bifidobacterium* NCIMB 41003.

At least one of the *Bifidobaceterium* strains may be in the form of viable cells.

At least one of the *Bifidobaceterium* strains may be in the form of non-viable cells.

In some cases, the *Bifidobacterium* strain NCIMB 41676 is present in the formulation in an amount of more than $10^6$ cfu. The *Bifidobaceterium* strain NCIMB 41676 may be present in the formulation in an amount of about $5 \times 10^8$ cfu.

In some cases, the *Bifidobacterium* strain NCIMB 41003 is present in the formulation in an amount of more than $10^6$ cfu. The *Bifidobaceterium* strain NCIMB 41003 may be present in the formulation in an amount of about $5 \times 10^8$ cfu.

Bacterial viability reflects the number of culturable bacteria within a sample, i.e. the number of bacteria which retain the ability to reproduce when grown under optimal conditions (Viable cells). Put another way viability reflects the number of individual bacterial cells which retain the ability to replicate into larger bacterial colonies (colony forming units (CFUs)).

Viability is commonly determined using plate-counting methods, whereby a bacterial sample is diluted and then incubated on an agar plate containing the necessary nutrients for growth. Viability is then calculated from the number of bacterial colonies identified on a plate. Such methods are summarized in Modern Food Biology 2005 $7^{th}$ edition, James Monroe Jay, Martin J. Loessner, David A. Golden, Springer Science, New York.

Whilst plate-counting gives a good indication of viability, it does not encompass all living bacterial cells in the sample. (Kell, Douglas B., et al. 1998).

Samples will also contain "viable but non-culturable" (VBNC) cells which remain metabolically active but have lost the ability to replicate at the time of analysis by plate count, and thus despite being alive will not form CFUs. Finally, samples will also contain dead cells. These two groups can be grouped together as "Non-Viable cells". Therefore Non-viable cells are the inverse of Viable cells i.e. all those cells which have lost the ability to replicate when tested.

All samples containing Viable cells will also contain Non-Viable cells, therefore the definition of a Viable cell culture is clarified using CFU measurements.

All Non-Viable samples will contain at least VNBCs and possibly small amounts of Viable cells. Industry standard lower level detection limits of $10^3$ CFU/g viable cells allow for the inherent process variability caused by the presence of a certain number of VBNCs/Viable cells in Non-Viable samples.

In some embodiments, such as, but not limited to, special sterile food products or medicaments a non-replicating form of a probiotic strain may be preferable. For example, at least 95%, preferably at least 97%, more preferably at least 99% of the *Bifidobacteria* strain can be non-replicating in the composition.

The formulation may be in the form of a bacterial broth, or in the form of a freeze-dried powder.

In some cases, the formulation further comprises a prebiotic material.

In some cases, the formulation further comprises an ingestible carrier.

The ingestible carrier may be a pharmaceutically acceptable carrier such as a capsule, tablet or powder.

The ingestible carrier may be a food product such as acidified milk, yoghurt, frozen yoghurt, milk powder, milk concentrate, cheese spreads, ice cream, dressings or beverages.

The formulation in some cases is in the form of a fermented food product or a fermented milk product.

In some cases, the carrier does not occur in nature.

The formulation may comprise a protein and/or peptide, in particular proteins and/or peptides that are rich in glutamine/glutamate, a lipid, a carbohydrate, a vitamin, mineral and/or trace element.

The formulation may comprise an adjuvant.
The formulation may comprise a bacterial component.
The formulation may comprise a drug entity.
The formulation may comprise a biological compound.

Also provided is a foodstuff comprising a formulation of the invention.

Also provided is a medicament comprising a formulation of the invention.

The invention also provides use of an isolated strain of *Bifidobacterium* NCIMB 41676 in combination with an isolated strain of *Bifidobaceterium* NCIMB 41003 in the prophylaxis or treatment of irritable bowel syndrome (IBS).

The combination may:
  alter bowel symptoms associated with IBS;
  improve mood associated with IBS;
  reduce stress associated with IBS;
  reduce anxiety associated with IBS;
  improve sleep quality associated with IBS;
  treat depression associated with IBS; and/or
  normalise dysregulated cortisol awakening response associated with IBS The use may comprise administering a formulation of the invention.

Also provided is a combination product comprising an isolated strain of *Bifidobacterium* NCIMB 41676 and an isolated strain of *Bifidobaceterium* NCIMB 41003 for use in the prophylaxis or treatment of irritable bowel syndrome (IBS). The combination product is described herein.

The effect on sleep is particularly important. Sleep disturbances are observed at any stage of the life. These disturbances are typically characterized by a decrease in the ability to initiate and maintain sleep, and by a reduced proportion of the deeper, more restorative sleep. Quality of life is substantially impaired in individuals suffering from those alterations.

Infant sleep normally changes over the first months of life to follow a diurnal rhythm with sleep lasting for a long unbroken period at night and, similarly, sleep states change from being equally distributed between REM (active) and NREM (quiet) sleep at birth to one third REM and two thirds NREM by 8 months of age. Any failure to successfully negotiate these changes in infancy can also have lasting effects on the sleep patterns of the child.

The most common sleep disturbances in infants and children are those related to wakefulness (i.e. either difficulties in settling at bedtime or failure to sleep through the night without interruptions). It has been estimated that these disturbances affect 15 to 35% of infants aged less than 24 months. Infant and child sleep disturbances inevitably lead to parental sleep disturbance and stress which may result inadequate child-parent interaction which in turn aggravates infant and child symptoms leading to a vicious circle.

At the other end of life normal aging is also accompanied by changes in the sleep quality, quantity, and architecture. Specifically, there appears to be a measurable decrease in the ability of the healthy elderly to initiate and maintain sleep, accompanied by a decrease in the proportion of the deeper, more restorative NREM sleep.

Sleep is particularly important in older people. Along with the physical changes that occur as we get older, changes to our sleep patterns are a part of the normal aging process. As people age they tend to have a harder time falling asleep and more trouble staying asleep than when they were younger. It is a common misconception that sleep needs decline with age. In fact, research demonstrates that our sleep needs remain constant throughout adulthood. Changes in the patterns of our sleep, "sleep architecture", occur as we age and this may contribute to sleep problems. Sleep occurs in multiple stages including dreamless periods of light and deep sleep, and occasional periods of active dreaming (REM sleep). The sleep cycle is repeated several times during the night and although total sleep time tends to remain constant, older people spend more time in the lighter stages of sleep than in deep sleep.

Many older adults, though certainly not all, also report being less satisfied with sleep and more tired during the day. Studies on the sleep habits of older Americans show an increase in the time it takes to fall asleep (sleep latency), an overall decline in REM sleep, and an increase in sleep fragmentation (waking up during the night) with age. The prevalence of sleep disorders also tends to increase with age. Research suggests that sleep disturbance among the elderly can in part be attributed to physical and psychiatric illnesses and the medications used to treat them.

In addition to changes in sleep architecture that occur as we age, other factors affecting sleep are the circadian rhythms that coordinate the timing of our bodily functions, including sleep. For example, older people tend to become sleepier in the early evening and wake earlier in the morning compared to younger adults. This pattern is called advanced sleep phase syndrome. The sleep rhythm is shifted forward so that 7 or 8 hours of sleep are still obtained but the individuals will wake up extremely early because they have gone to sleep quite early. The reason for these changes in sleep and circadian rhythms as we age is not clearly understood.

Environmental stressors can also be an issue. Exposure to stress negatively affects sleep and the sleep/wake cycle. For example, experiencing work-related stressors having low social support, or exposure to trauma/combat can all disrupt sleep and the sleep/wake cycle.

Clinical trials in sleep medicine cover a wide range of sleep-wake problems, and accordingly the selection of outcome measures in sleep medicine clinical trials needs to be tailored to the specific disorder under examination. The investigator needs to consider the relative merits choosing a self-report questionnaire versus a physiologic test. Surprisingly, the self-report measures are often more sensitive to treatment effects as compared with more expensive physiologic tests.

In some cases the combination product may be used in a formulation suitable for ingestion by a companion animal such as a dog or a cat. One such formulation is a dry pet food which may include any one or more of a carbohydrate source, a protein source and a lipid source.

BRIEF DESCRIPTION OF THE FIGURES

The invention will be more clearly understood from the following description thereof, given by way of example only, with reference to the accompanying figures in which:

FIGS. 8(a) and (b) are bar charts of % decrease in HADS depression for the IBS patients before and after Bif35624 alone compared to before and after the combo treatment;

DETAILED DESCRIPTION

Figure 1:
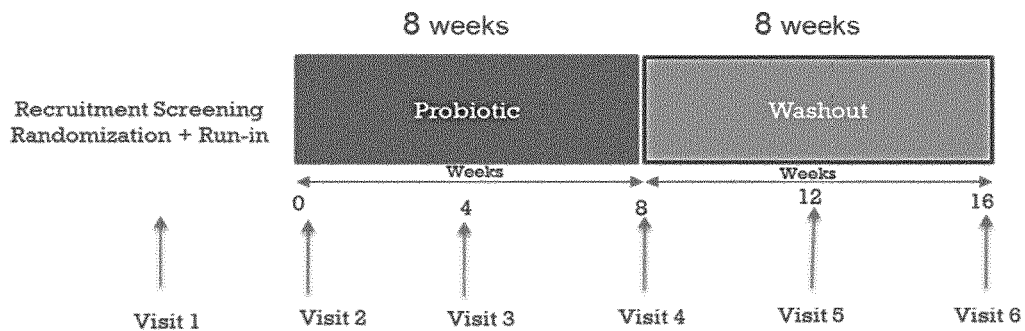
FIG. 1 is a schematic diagram of an open label combo IBS study schematic.

A deposit of *Bifidobacterium longum* strain UCC35624 was made at the National Collections of Industrial and Marine Bacteria Limited (NCIMB) Ferguson Building, Craibstone Estate, Bucksburn, Aberdeen, AB21 9YA, Scotland, UK on Jan. 13, 1999 and accorded the accession number NCIMB 41003.

*Bifidobacterium longum* strain UCC35624 was isolated from resected and washed human gastrointestinal tract. The strain is described in WO00/42168A, the entire contents of which are incorporated herein by reference.

*B. longum* 35624 has been extensively studied and shown to regulate inflammatory responses (Groeger et al., 2013, Konieczna et al., 2012) and reduce abdominal pain, bloating, gas and unpredictable bowel habits in IBS subjects in two well-controlled clinical studies (O'Mahony et al., 2005, Whorwell et al., 2006).

A deposit of *Bifidobaceterium longum* strain AH1714 was made at the National Collections of Industrial and Marine Bacteria Limited (NCIMB) Ferguson Building, Craibstone Estate, Bucksburn, Aberdeen, AB21 9YA, Scotland, UK on Nov. 5, 2009 and accorded the accession number NCIMB 41676.

*Bifidobacterium longum* strain AH1714 was isolated from colonic biopsy tissue from healthy human subjects. The strain is described in WO2011/058535A, the entire contents of which are incorporated herein by reference.

*B. longum* 1714 strain has been shown to attenuate the anxiety and stress and improve cognition in preclinical and clinical studies (Allen et al., 2016, Savignac et al., 2014, Savignac et al., 2015).

EXAMPLES

The following examples further describe and demonstrate embodiments within the scope of the invention. The examples are given solely for illustration and are not to be construed as limitations of the present invention, as many variations thereof are possible without departing from the spirit and scope of the invention.

Formulation

The strains may be administered in a single formulation which is preferred to ensure patient compliance. However, in some cases the strains may be administered at the same or different times and using the same or different routes for administration.

The strains may be administered in any suitable amount to achieve the desired result. In some cases, the same quantities of the strain are administered.

Preferably the strains are each administered at a dose of at least $10^6$ cfu per day per strain, preferably at a target dose of $5 \times 10^8$ cfu to $1 \times 10^9$ cfu per day per strain.

The strains are in the form of freeze dried powder which is blended with food grade excipient and filled into a format such as a sachet or capsule.

A freeze-dried powder comprising $5 \times 10^8$ CFU *B. longum* 35624 and $1 \times 10^9$ CFU *B. longum* 1714 was prepared. Strains were fermented in de Man, Rogosa and Sharpe medium (from first principles). The particulate collected after centrifugation of each strain was washed and subsequently freeze-dried.

Example 1

An Open Label Irritable Bowel Syndrome (IBS) Study: A Combination *B. longum* Product Shows Reduction in Symptoms of IBS in Adults (Combo)

A human trial was performed as follows to investigate the effect of a combination of *B. longum* 35624 and *B. longum* 1714 on bowel symptoms in adults with irritable bowel syndrome (IBS). The work consisted of an open label study. Bowel symptoms were measured using self-reported measures such as the IBS symptom severity scale (IBS-SSS) which incorporates pain, distension, bowel dysfunction and quality of life (global well-being). The IBS-SSS is recognised for its ability to reliably score patients previously classified as mild, moderate or severe. The maximum achievable score was 500. Recruitment of more homogeneous groups of patients (mild, moderate and severe cases) were indicated by scores of 75 to 175, 175 to 300 and over 300 respectively. Controls scored below 75 and patients scoring in this range can also be in remission. IBS-SSS of ≤50 has been defined as a clinically significant change in symptom severity (Francis et al., 1997). This scale provides a valuable instrument in helping to meet the many challenges offered by IBS.

The clinical protocol for this trial was as follows:

Forty female subjects aged 18-55 years were recruited with IBS, diagnosed by Rome III criteria, and mild to moderate anxiety and/or depression as determined by the Hospital Anxiety and Depression scale (HADs). Subjects who had a psychiatric diagnosis other than anxiety or depression, a major inflammatory disorder or were on antidepressants, anxiolytics or antipsychotics in the last 6 months were excluded.

Results of Combo Trial on IBS Symptoms as Measured by the IBS-SSS Scale

IBS symptoms were assessed by the IBS-Symptom Severity Scale (IBS-SSS). This was an open labelled study with a freeze-dried powder comprising $5\times10^8$ CFU *B. longum* 35624 and $5\times10^8$ CFU *B. longum* 1714 (combo) for 8-weeks, followed by an 8-week washout (FIG. 1) The IBS-SSS was measured at 0, 4, 8, 12 and 16 weeks.

Figure 2:
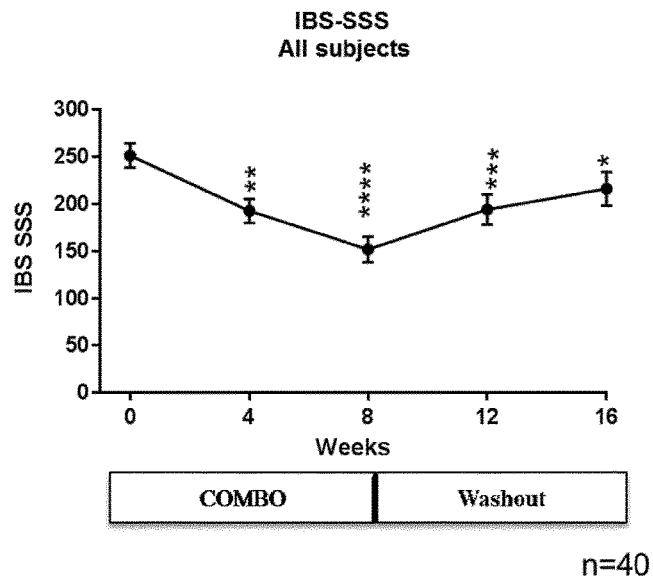
FIG. 2 is a graph of IBS symptom severity scale (IBS-SSS) for the IBS patients before and after combo treatment.
Figure 3:
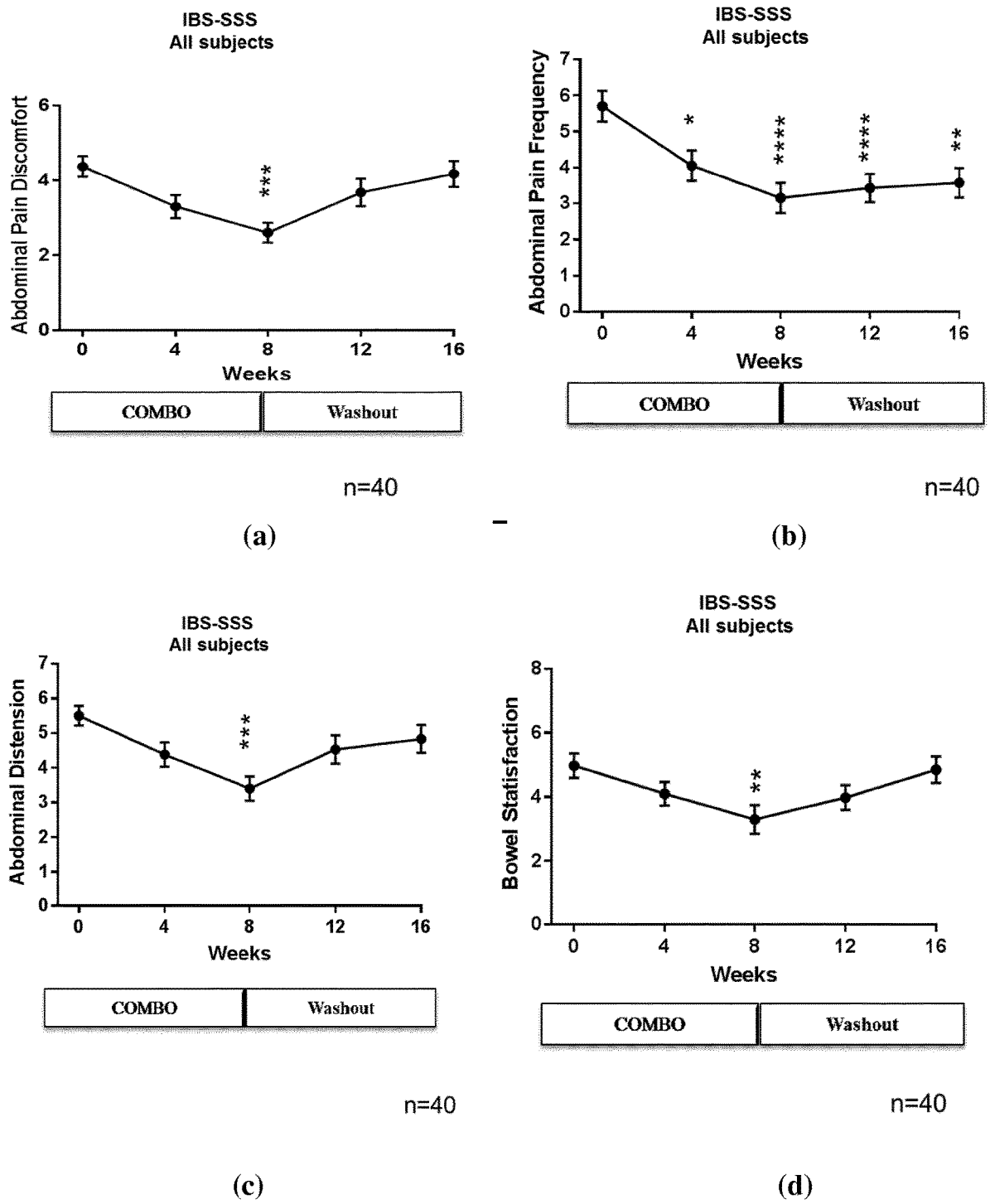
FIGS. 3(a) to (e) are a set of graphs of IBS-SSS individual symptoms (Abdominal pain (a) discomfort and (b) frequency, (c) abdominal distension, (d) bowel satisfaction and (e) IBS quality of life) for the IBS patients before and after combo treatment.
Figure 3:
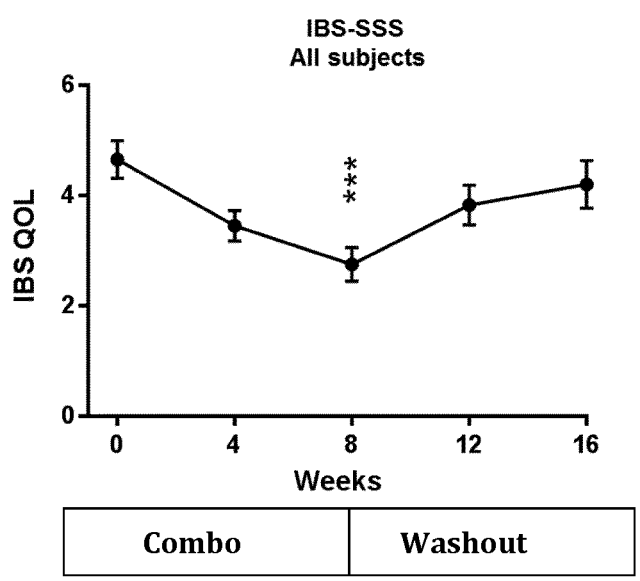
Figure 4:
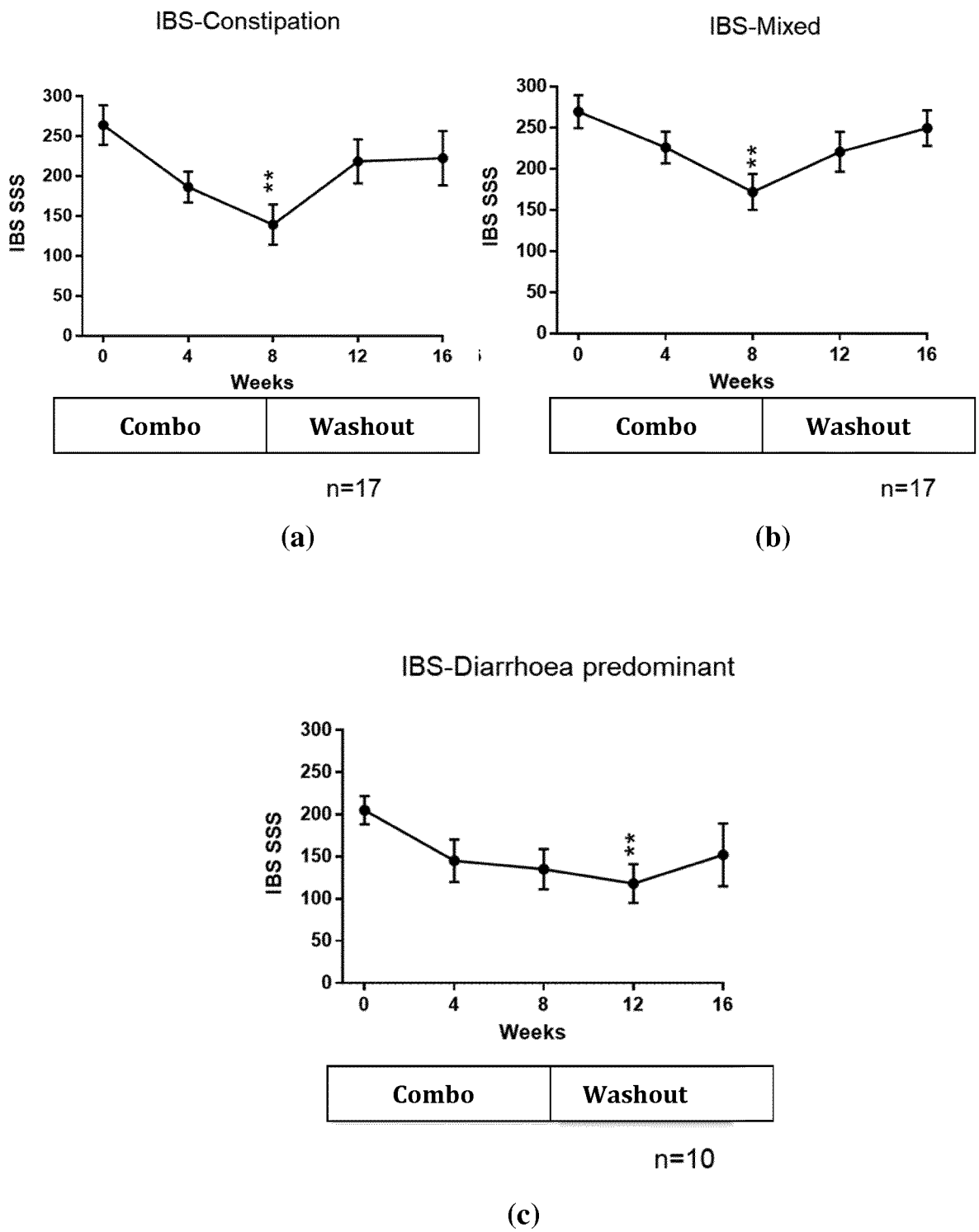
FIGS. 4(a) to (c) are a set of graphs of IBS symptom severity scale (IBS-SSS) for the IBS patients (constipation (a), mixed (b) and diarrhoea (c)) before and after combo treatment.
Figure 5:
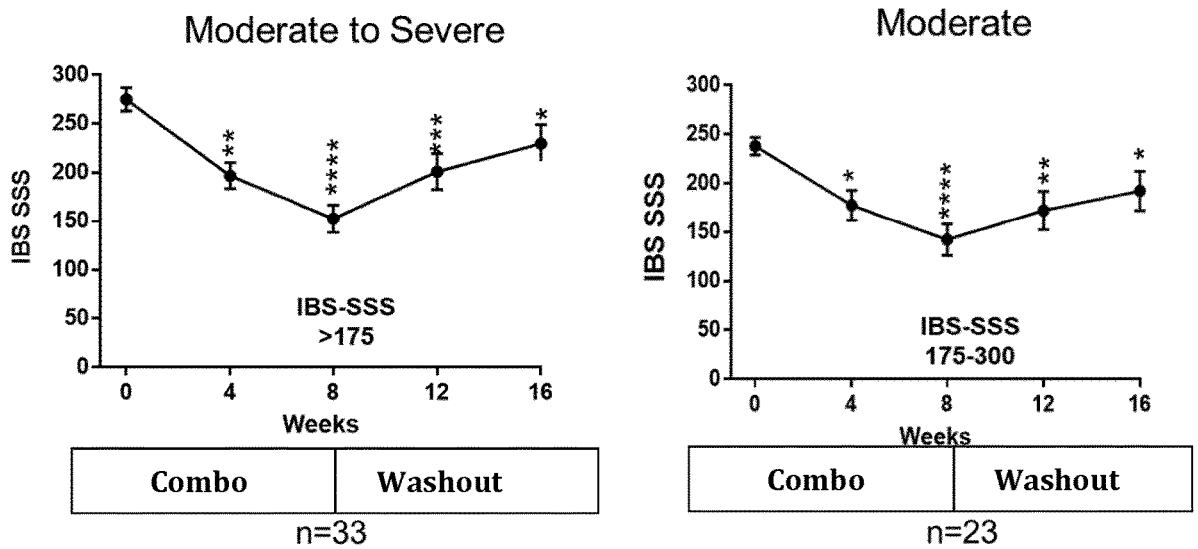
FIGS. 5(a) to (c) are a set of graphs of IBS symptom severity scale (IBS-SSS) for the IBS patients ((a) moderate to severe, (b) moderate and (c) severe) before and after combo treatment.
Figure 5:
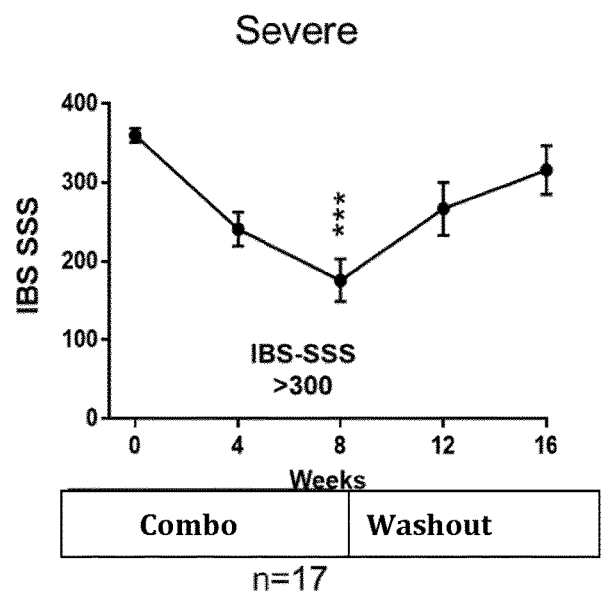

The IBS-SSS scores improved significantly from baseline to the end of the intervention (8 weeks) by a mean± SD of 100± 112.5 in the combo group. However once feeding stopped the IBS-SSS dis-improved again and by week 16 (8 weeks post feeding) with only an improvement of 35± 97 from baseline. A clinically important difference has been described as a change in IBS-SSS of ≥50 (FIG. 2). When we analysed all the individual symptoms that make up the IBS-SSS score the combo treatment improved all symptoms including of these including abdominal pain discomfort, abdominal pain frequency, abdominal distension, bowel satisfaction and IBS quality of life, a result which is not the same for all probiotics (FIGS. 3(*a*)-(*e*)). The combo product benefits all subtypes of IBS patients including those with constipation, diarrhoea and mixed patients (FIGS. 4(*a*)-(*c*)). The combo product impacts even the most severe patients while feeding but symptoms start to return once the combination is not being consumed anymore (FIGS. 5(*a*)-(*c*)).

Normally randomised double-blind placebo-controlled studies are state of the art in clinical medicine but using the open label study we were able to provide valuable information on estimating the carryover effect, determine the washout period, provide reliable data on the subject characteristics and variation in the parameters measured as well as showing the therapeutic potential of this combination product.

Results of Combo Trial on IBS Symptoms as Measured by the HADs Scale

Figure 6:
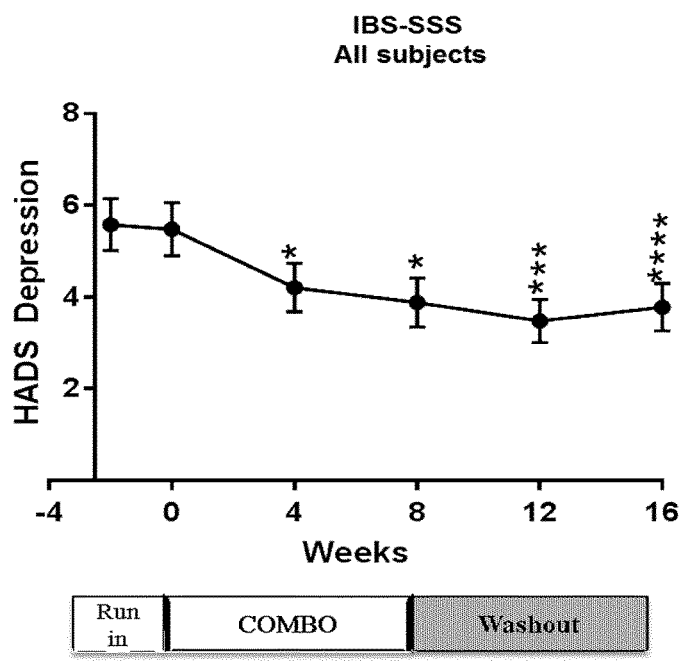
FIGS. 6(a) and (b) are graphs of (a) HADS depression and (b) HADS anxiety scores for the IBS patients before and after combo treatment.
Figure 6:
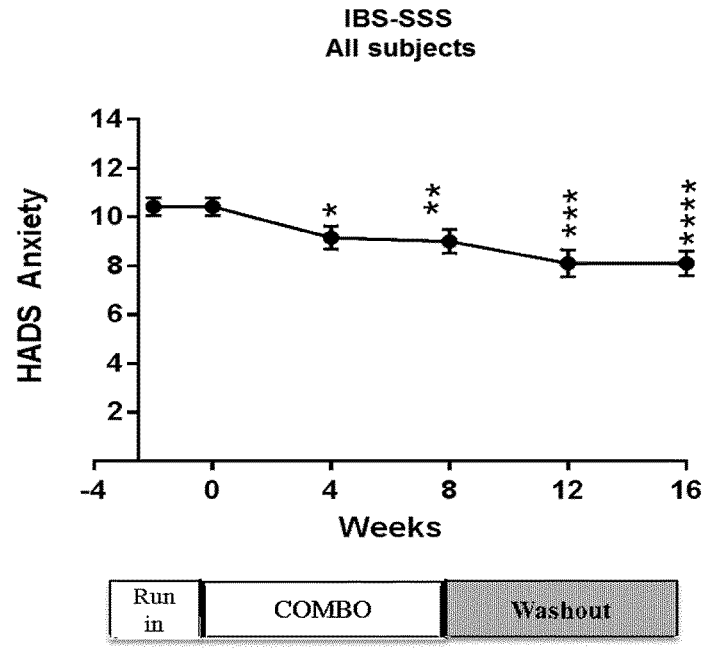

In the Combo trial we measured anxiety and depression using a validated questionnaire called the Hospital Anxiety and Depression scale (HADs) at 0, 4, 8, 12 and 16 weeks. We found that *B. longum* 35624 in combination with *B. longum* 1714 was very effective in IBS in reducing depression and anxiety symptoms in IBS subjects. The HADs depression score improved significantly from baseline to the end of the intervention (8 weeks) by a mean±SD of −1.6± 3.122 in the combo group. Surprisingly once feeding stopped the HADs depression score improved further at week 12 (−2.0± 2.63; mean±SD) and maintained this improvement by week 16 (−1.75± 3.386; mean±SD) (8 weeks post feeding) (FIG. 6(*a*)). The HADs anxiety score improved significantly from baseline to the end of the intervention (8 weeks) by a mean±SD of −1.375± 3.012 in the combo group. Surprisingly once feeding stopped the HADs anxiety score also improved further at week 12 (−2.275± 3.637; mean±SD) and maintained this improvement at week 16 (−2.3± 2.98; mean±SD) which was 8 weeks post participants stopped taking the combo product. (FIG. 6(*b*)). A clinically important difference has been described as an HADs improvement of ≥2.

No Correlation at Baseline Between HADS Scores and Symptom Severity Score in IBS Patients in the Combo Study IBS is a Gut-Brain Disorder. It well recognized that anxiety and depression are commonly encountered co-morbidities among sufferers with IBS. However, little is known of the precise nature of these co-morbidities and their association in IBS. The objective was to characterize the relationship between IBS and these psychiatric co-morbidities in the IBS group with elevated anxiety and depression to see if these were dependent or independent cofactors. This was assessed utilising the baseline results of the combination study, as described in example 1.

Figure 7:
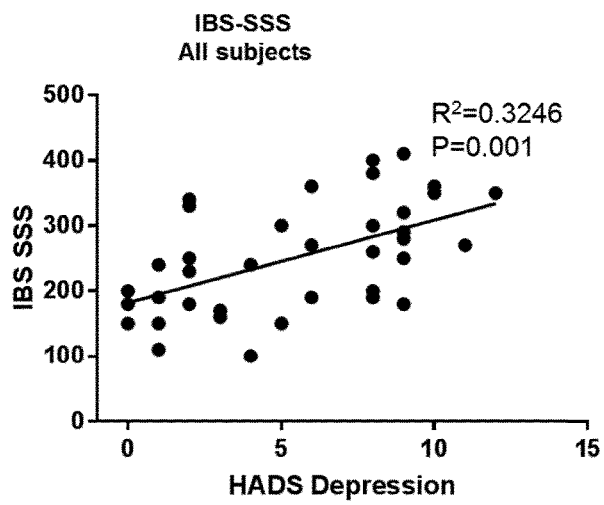
FIGS. 7(a) and (b) are plots of the correlation between (a) IBS symptom severity scale vs HADS depression and (b) IBS symptom severity scale vs HADS anxiety.
Figure 7:
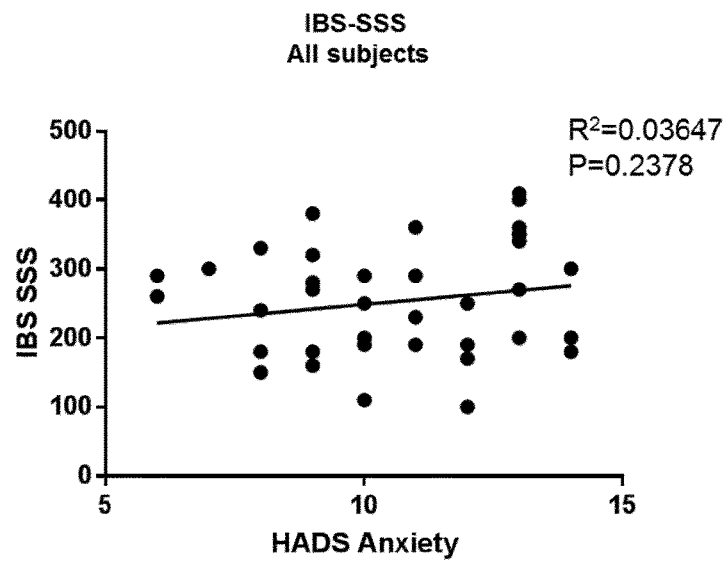
Figure 9A:
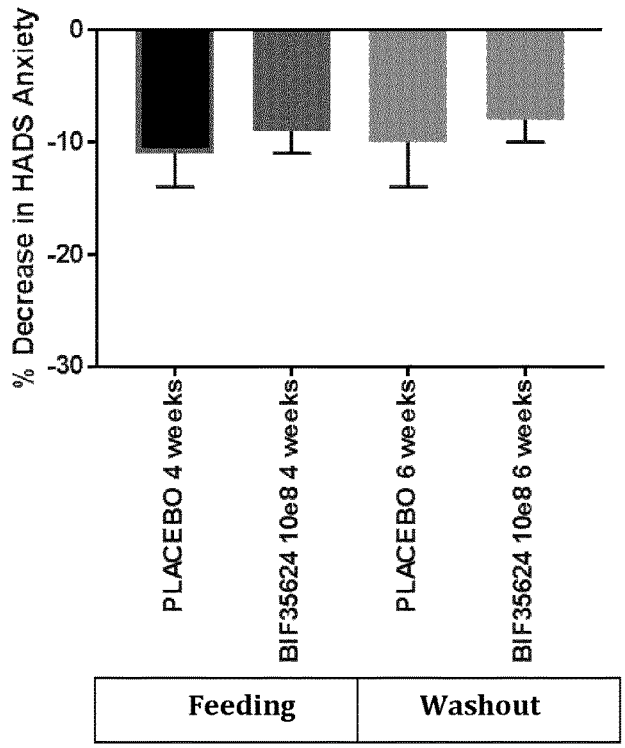
FIGS. 9(a) and (b) are bar charts of percent decrease in HADS anxiety and depression scores for the IBS patients before and after Bif35624 alone compared to before and after the combo treatment.
Figure 9B:
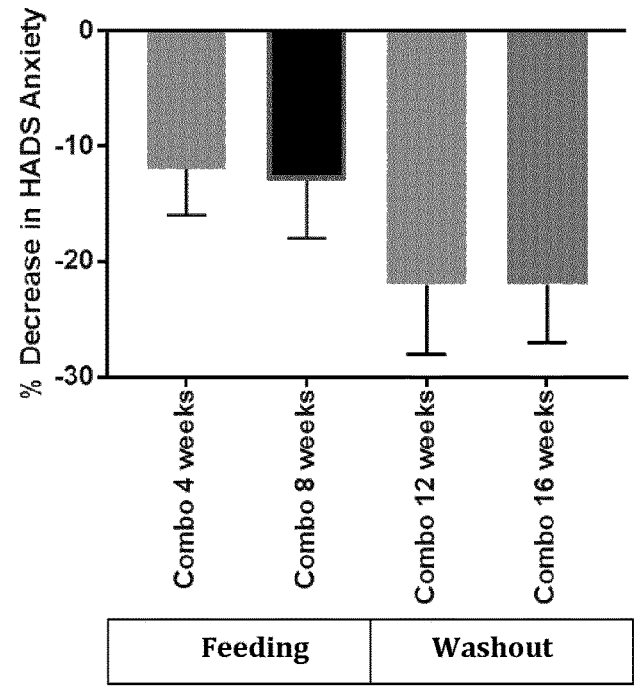

The median IBS-SSS score was 250 (IQR: 190-315) while HADs anxiety score and HADs depression score were 10.43± 2.3 and 5.48± 3.69 respectively. Of the 40 subjects, 95% and 45% had a HADs anxiety or HAD depression score of >8 respectively, while 38% had both a HADs anxiety and HADs depression score of >8. Correlation analysis of the IBS-SSS to the HADs depression and HADs anxiety scores showed a weak correlation for HADs depression score ($R2=0.3246$; $P=0.001$) but no correlation for HADs anxiety score ($R2=0.3647$; $P=0.2378$) (FIGS. 7(*a*)-(*b*)). For the group of IBS subjects with mild to moderate levels of anxiety and depression, a weak or no correlation was observed between the severity of IBS and the levels of anxiety and depression. These results suggest that IBS and co-morbid anxiety/depression are independent factors and may require separate management approaches as used in the combination 35624/1714 product. To further interrogate this hypothesis the results of the combination trial were assessed by reference to data gathered using 35624 strain alone.

Comparison of the Effect of the Combo or 35624 Alone has on the HADS Scores of IBS Patients The Combo product had a clinically significant effect in improving mood (reducing anxiety and depression) and surprisingly, the effects on anxiety and depression were sustained during the 8-week period where participants did not take the combo product. Therefore, it was of interest to compare our results to a previous study performed in IBS patients who were treated with *B. longum* 35624 alone (Whorwell et al 2006). This study was a randomised double-blind placebo controlled multicentre trial where all types of IBS patients, whether they had co-morbid anxiety/depression, were accepted into the trial. There was no effect on HADs scores over the placebo effect with the single strain *B. longum* 35624. The subjects had a transient decrease in severity of HADS scores which disappeared once feeding stopped (FIGS. 8(*a*) and 9(*a*)). This differs from the combo product where the significant effect on HADs scores were seen after feeding was potentiated and the effects maintained 8 weeks post cessation of feeding (FIGS. 8(*b*) and 9(*b*)).

Example 2

The Effect of Feeding of 35624® Strain Alone or in Combination with 1714™ Strain on the Plasma TNF-a Levels in IBS Patients After feeding the combo product to IBS patients we found there was a reduction in anxiety and depression with IBS and these effects sustained post cessation of feeding. To determine if there was also a change in inflammatory tone of the study participants the plasma biomarker tumor necrosis factor (TNF)-α was measured. In a recent study, TNF-α serum levels were correlated with discomfort and severity of symptoms in IBS patients (Choghakhori et al 2017). Several other studies have established that IBS patients had higher levels of TNF-α in serum compared to healthy controls (Rana et al 2012; Seyedmirzaee et al 2016; Schmulson et al 2012). Furthermore, in a case-control trial, the authors demonstrated that abnormal levels of cytokines including tumor necrosis factor-α, were significantly correlated with the symptoms of IBS, and with the severity of depressive and anxiety mood symptoms (Zhen et al 2018).

We investigated the effect of the combination of *B. longum* 35624 and *B. longum* 1714 on the inflammatory marker TNF-α in adults with IBS at 0, 4, 8, 12 and 16 weeks.

The results were compared to another clinical trial undertaken to study the effect of *B. longum* 35624 alone on patients with IBS who were comorbid with anxiety and depression and who had similarly consumed the product for 8 weeks. For this study, there was a 4-week washout period. The test groups were: Placebo (n=31) and *Bifidobaceterium longum* 35624 (1×10$^{10}$ cfu) (n=39).

Plasma samples were collected from peripheral blood and stored at −80° C. until analysis. TNF-α in the plasma were assayed using a 96-well assay kit from Meso Scale Discovery (Gaithersburg, Md.; catalog K15008B-1), and was quantitated and reported as change from baseline in picograms per millilitre. Each sample was assayed in duplicate.

Figure 10:
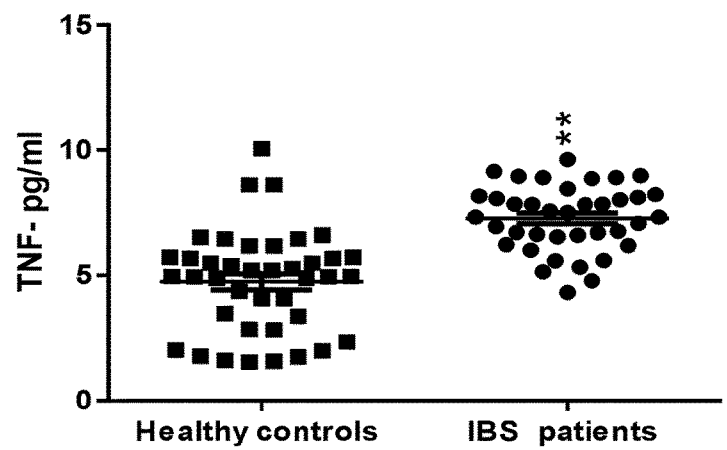
FIGS. 10(a) and (b) are plots of plasma TNF levels for the Healthy vs. IBS patients and IBS patients before and after combo treatment.
Figure 10:
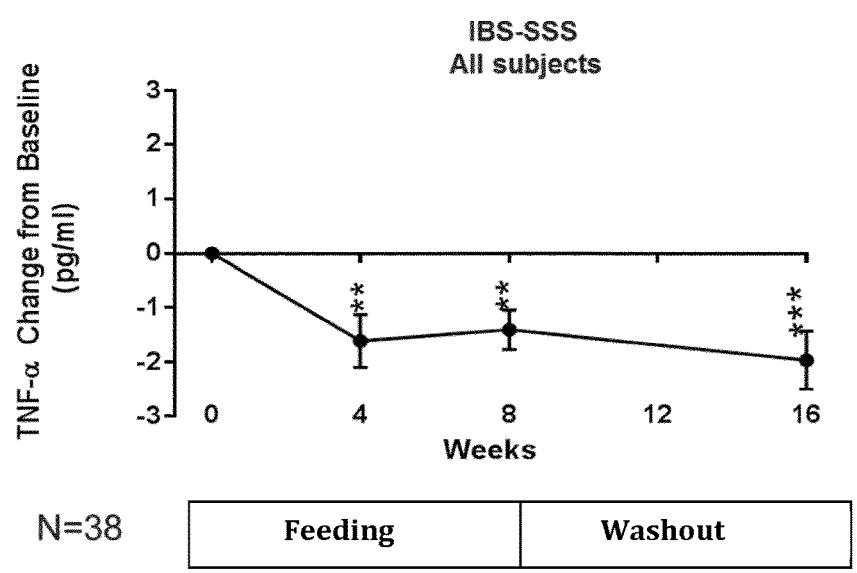
Figure 11:
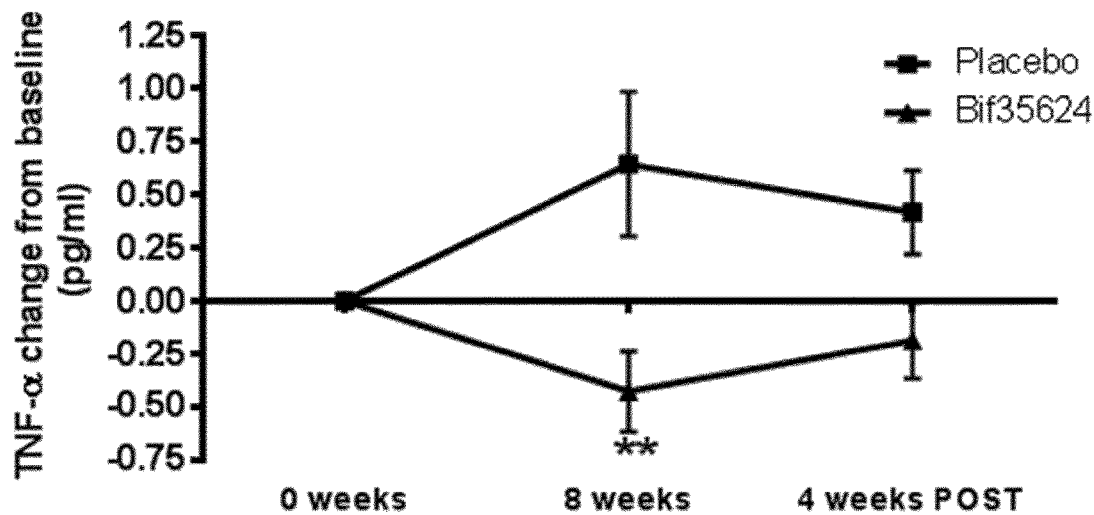
FIG. 11 is a plot of plasma TNF levels for the IBS patients before and after Bif35624 treatment.

In agreement with previous reports we also found a significant increase in plasma TNF-α in our IBS patients compared to healthy controls (FIG. 10(*a*)). The combo product decreased plasma TNF-α significantly over time in the IBS cohort. Again, similar to what we saw with the HADs scores there was a prolonged (8 weeks) improvement post feeding i.e. a decrease in TNF-α even after feeding had stopped (FIG. 10(*b*)). In a previous study where IBS patients was fed *B. longum* 35624 alone there was a significant decrease in plasma TNF-α compared to placebo during the feeding period of 8 weeks but 4 weeks after end of feeding the plasma TNF-α levels were increasing and returning to baseline levels (FIG. 11). This again highlights a synergy between the combination of *B. longum* 35624 and *B. longum* 1714 where we get a prolonged improvement after feeding has stopped. In comparison *B. longum* 35624 loses its anti-inflammatory effect once feeding stops.

Example 3

Results of Trial on Sleep Quality as Measured by the Pittsburgh Sleep Quality Index Sleep quality of IBS patients were assessed by the Pittsburgh Sleep Quality Index (PSQI). This was an open labelled study with the 'COMBO' (5×10$^8$ CFU/day *B. longum* 35624+1×10$^9$ CFU/day *B. longum* 1714), sachet format with maltodextrin and a flowability agent such as silicon dioxide was taken for 8-weeks, followed by an 8 week washout (FIG. 1). The PSQI was measured at 0, 4, 8, 12 and 16 weeks. Sleep quality was assessed through a modified PSQI designed to measure sleep quality and disturbance over the past month in clinical populations as it has acceptable reliability and validity (Buysse et al., 1989). The PSQI is a 19-item self-report measure assessing sleep quality across seven domains: 1) sleep duration, (2) sleep disturbance, (3) sleep latency, (4) daytime dysfunction due to sleepiness, (5) sleep efficiency, (6) overall sleep quality, and (7) sleep medication use. Each of the sleep components yields a score ranging from 0 to 3, with 3 indicating the greatest dysfunction. The sleep component scores are summed to yield a total score ranging from 0 to 21 with the higher total score (referred to as global score) indicating worse sleep quality. In distinguishing good and poor sleepers, a global PSQI score>5 yields a sensitivity of 89.6% and a specificity of 86.5%.1 (Buysse et al., 1991; Herman et al., 2002; Fillingim et al.; 2011, Porto et al., 2011). We used this >5 global PSQI cut off to look at a subpopulation of our IBS patients who have poor sleep quality. Subjective sleep quality is scored as follows 'very good' (0,) 'fairly good'(1), 'fairly bad' (2) 'very bad' (3).

Figure 12A:
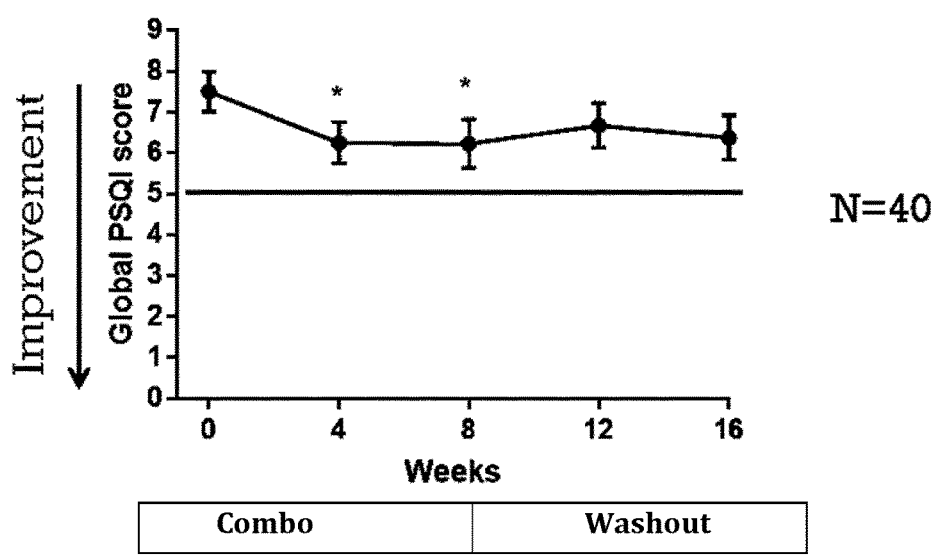
FIG. 12 is a plot of global PSQI score for the IBS patients (a) and IBS patients (PSQI over 5) (b) before and after combo treatment.
Figure 12B:
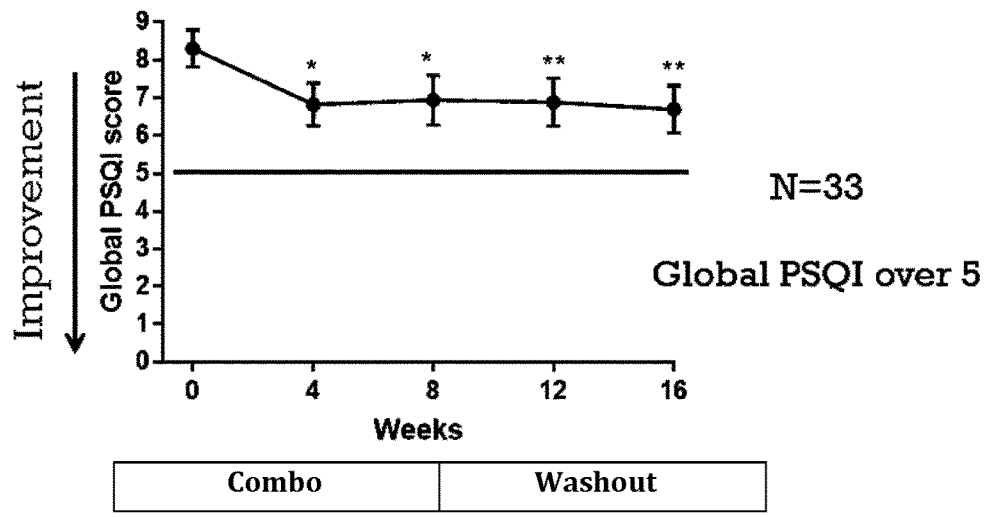
Figure 13:
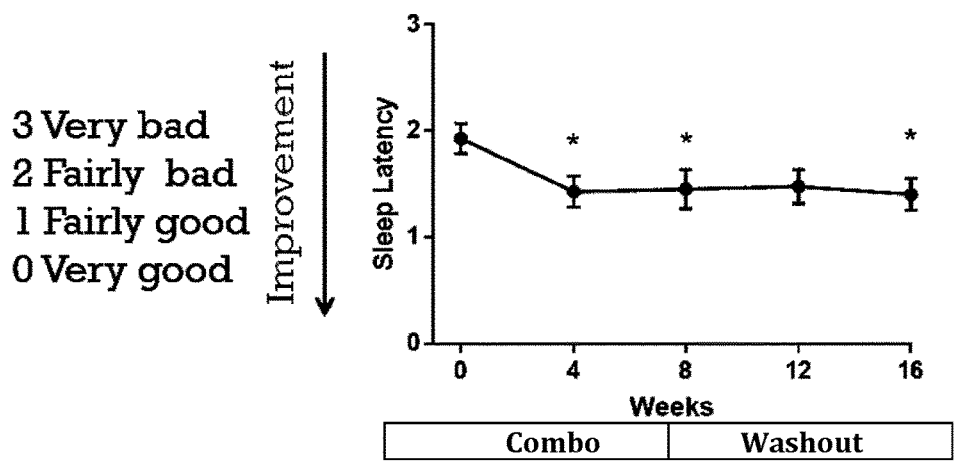
FIG. 13 is a plot of subjective sleep latency for the IBS patients (a) and IBS patients (PSQI over 5) (b) before and after combo treatment.
Figure 13:
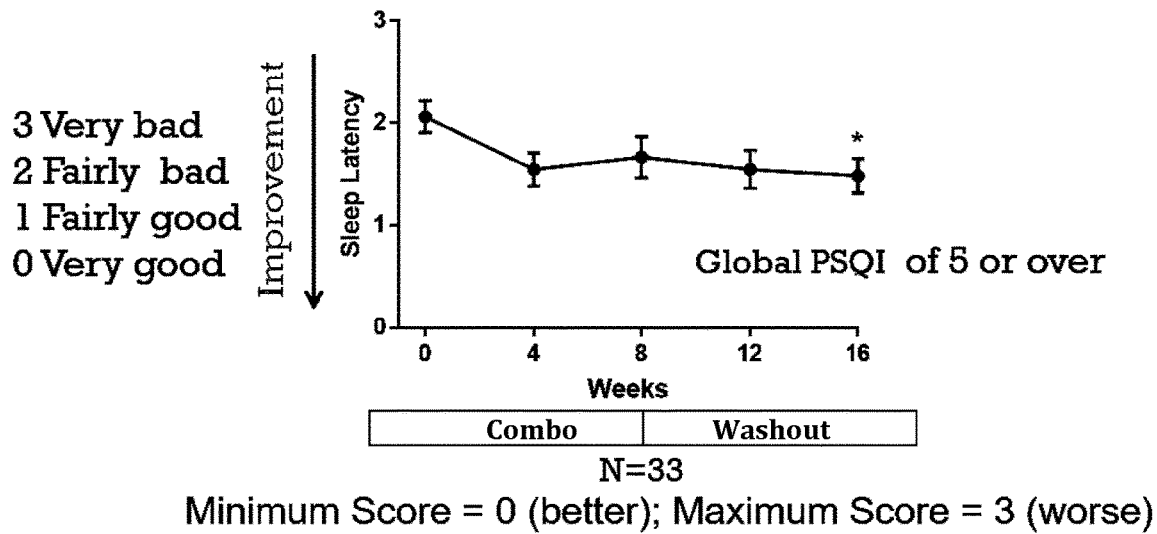
Figure 14:
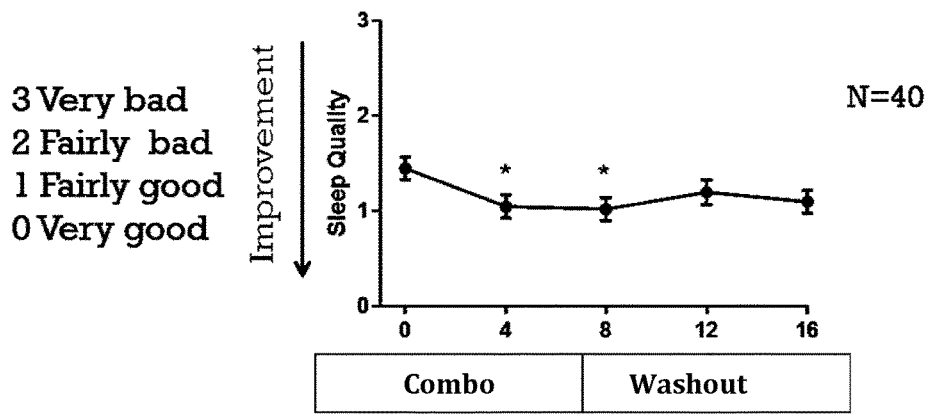
FIG. 14 is a plot (a) and table (b) of subjective sleep quality for the IBS patients before and after combo treatment.
Figures 14, 15:
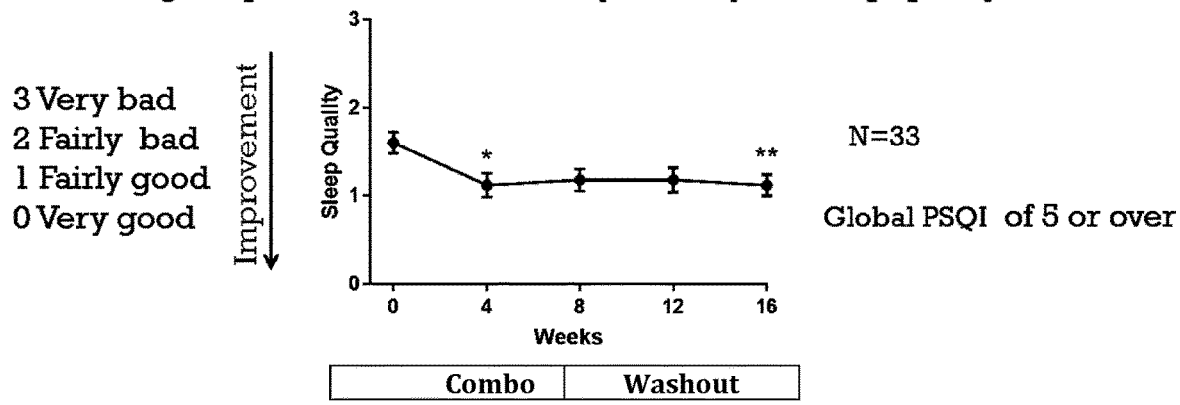
FIG. 15 is a plot (a) and table (b) of subjective sleep quality for the IBS patients (PSQI over 5) before and after combo treatment.

The daily ingestion of the Combo product significantly decreased PSQI global scores at week 4 and week 8 (FIG. 12(*a*)). A decrease in PSQI global score indicates an improvement in sleep quality. When looking at a sub-group of IBS patients who had poor sleep quality (>5 global PSQI) the Combo significantly decreased PSQI global scores at all time points even those post feeding (FIG. 12(*b*)). The global PSQI score is the sum of seven component scores (sleep disturbance, overall sleep quality, sleep latency (time to fall asleep), duration of sleep, daytime dysfunction due to sleepiness, sleep efficiency, and need for medicines to sleep). Among them, the combo significantly decreased the PSQI-sleep latency score at week 4 and week 8 and 8 weeks post feeding (FIG. 13(*a*)). Again, when we looked at a sub population of "bad sleepers" we saw a decrease in PSQI-sleep latency at 8 weeks post feeding (FIG. 13(*b*)). Another notable result was that when subjects were asked the question 'during the past month, how would you rate your sleep quality overall?), the results showed that administration of the Combo product significantly improved sleep quality in agreement with the PSQI global score. Subjective sleep quality scores improved from baseline to the end of the intervention (8 weeks), in the combo group and maintained their effect after feeding had stopped (16 weeks) (FIG. 14(*a*)). When looking at percentage of the different categories of sleepers the combo treatment increased the number of patients describing their sleep as 'good' and decreasing the number of subjects who had 'fairly bad' sleep and this is maintained even after the feeding has stopped (FIG. 14 (*b*)). We also analysed a sub group of IBS patients who had reported that they had 'bad' sleep at baseline, and this was reflected in a global score of PSQI of greater than 5. Subjective sleep quality scores improved from baseline to the end of the intervention (8 weeks) in the this group (global PSQI score of over 5) and maintained their effect after feeding had stopped (16 weeks) (FIG. 15 (a)). When looking at percentage of the different categories of sleepers the combo treatment increased the number of patients describing their sleep as 'fairly good' and decreasing the number of subjects who had 'fairly bad' sleep and this is maintained even after the feeding has stopped (FIG. 15(b)). The beneficial effect of combo product on sleep quality is indicative of the potential benefits of this strain combination for health promotion.

In this IBS study 33 of the 40 patients had a global PSQI score of 5 and over and have so been characterised as bad sleepers which agrees with the literature which shows that IBS patients have poor sleep quality. After combo administration there was a significant reduction in the bad sleep quality as measured by the PSQI in these IBS patients and this effect is maintained 8 weeks after the combo administration. These results agree with what we have seen with the HADs scores where the effects maintained 8 weeks post cessation of feeding as there is an interaction between IBS symptoms and poor sleep quality.

Example 4

The Effect of Feeding of 35624 Strain in Combination with 1714 Strain on Salivary Cortisol in IBS Patients As part of the open label trial (as described in example 1), we investigated the effect of a combination of *B. longum* 35624 and 1714 strains on the stress hormone cortisol in adults with IBS at 0, 4, 8, 12 and 16 weeks. Saliva cortisol and the cortisol awakening response is non-invasive, easy to perform and a well-validated method to assess HPA axis functioning. As salivary cortisol is circadian, we measure waking cortisol at 4 different time points (15 minutes, 30 minutes, 45 minutes, 60 minutes). The dynamic rise in morning cortisol usually occurs within 30-45 minutes after awakening before progressively dropping over the remainder of the day. This is known as the Cortisol Awakening Response (CAR). A normal CAR response is characterised by a short-lived peak at 30 minutes. In IBS patients this dynamic response is 5 blunted with little or no change in cortisol levels on awakening. It is hypothesised that this is due to chronic stressors, associated with the IBS condition, inducing an "exhaustion" or negative feedback loop in the CAR response. A normalisation of the CAR response could indicate a beneficial reduction in the impact of IBS on the normal working of the brain-gut axis of the subject.

For hygienic collection of saliva samples Salivette swabs are used, then samples are kept frozen at −80° C. until assay. The Salivette sampling device consists of cotton swabs which the patients chew for 2 minutes and then they are transferred to the plastic tube of the device. The patient is instructed to refrain from eating, smoking, drinking tea or coffee, or brushing teeth 15 min prior to sampling and no dental work is allowed in the 24 hours preceding sample collection. Saliva samples can be stored at room temperature or in the participants' home refrigerator or freezer until they are delivered to the lab. Cortisol concentrations were determined using the Cortisol Enzyme Immunoassay Kit according to the manufacturer's instruction (Enzo Life Sciences, UK). The assay detection limit was 0.16 nmol/l. Inter- and intra-as say coefficients of variation (CVs) were 11.24% and 8.2% respectively.

From the literature subjects with IBS exhibit high cortisol levels at awakening and a blunted CAR i.e. minimal or no increase in cortisol at 30 minutes after awakening and therefore no subsequent decrease at 60 minutes. To best visualise the effect of an intervention on the CAR, the increase in the "area under the curve" ($AUC_i$) is graphed and calculated. The $AUC_i$ is the area that can be measured underneath the response curve from time zero to time 60 minutes. It is calculated with reference to the first value thereby emphasizing the changes over time.

Figure 16:
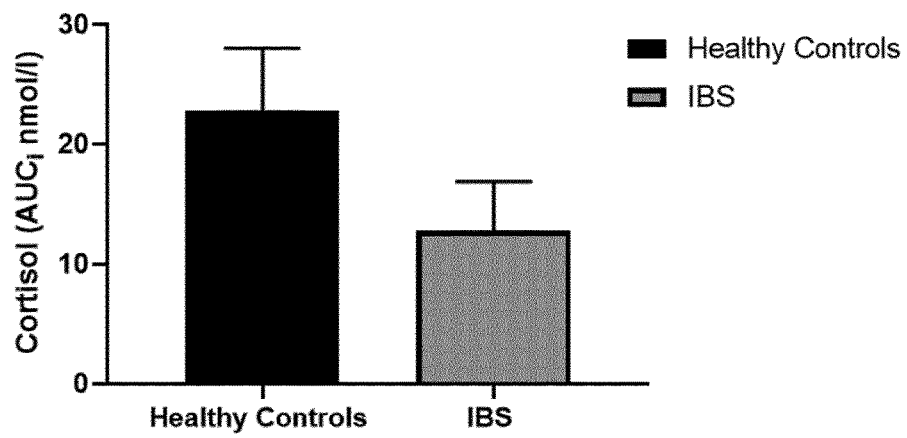
FIG. 16 is a bar graph of salivary cortisol ($AUC_i$) for the Healthy Controls vs. IBS patients.

IBS patents have a blunted increase in cortisol production upon waking in the morning which results in a lower AUCi for basal morning salivary cortisol levels in IBS subjects in comparison to healthy controls (FIG. 16). This graph was recreated from data provided in the publication Suarez-Hitz et al. 2012.

Figure 17:
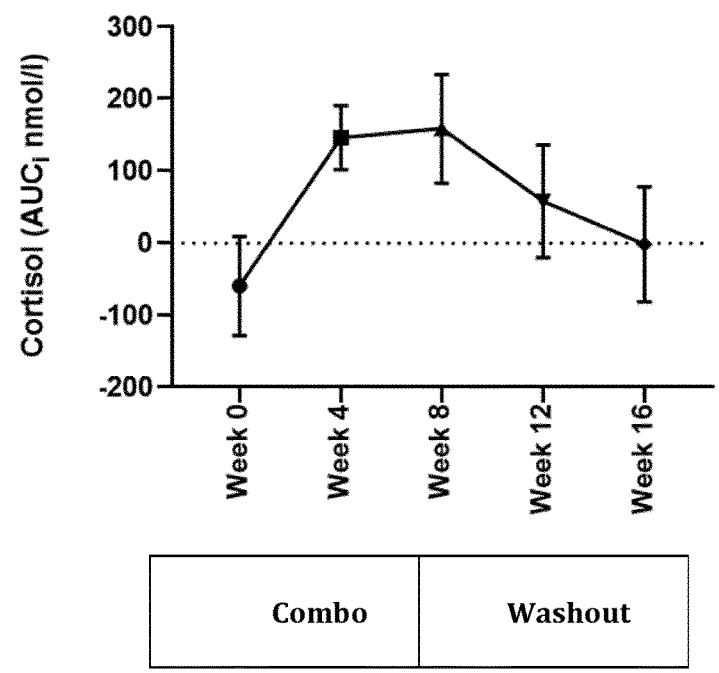
FIG. 17 is a plot of salivary cortisol ($AUC_i$) for the IBS patients (moderate to severe) before and after combo treatment.

The use of the combination of *B. longum* 35624 and *B. longum* 1714 (Combo) had a normalising effect on the production of awakening cortisol, leading to a temporary increase at 30 mins post wakening in adults with moderate and severe symptoms of IBS. When the AUCi (n=33) was measured at week 0, week 4, week 8, week 12, and week 16 the AUCi increased, indicating a reversal of the blunting of the CAR response in IBS subjects during feeding. This effect was lost over the following 8 weeks post-feeding (week 9-16) (FIG. 17). Therefore, the feeding of the Combo normalises the dysregulated cortisol awakening response. This effect unlike the effect on sleep quality, anxiety and depression, was not sustained after feeding. To our knowledge no probiotic or probiotic combination has been seen to alter the CAR in IBS subjects in this beneficial fashion.

Example 5

Demonstration of Strain Compatibility In Vitro: Overnight Cultures of 35624 Either Alone or in Combination with 1714™ strain, or DPC6315 strain Prior to carrying out the human trial two co-culture experiments were done to investigate the effect of a combination of *B. longum* 35624 with another *B. longum* DPC6315 or 1714 strain in growth experiments. All past experience growing the 35624 strain has indicated that it is a sensitive strain that requires careful management. *B. longum* DPC6315, was chosen for its anti-inflammatory tone in in vitro experiments (example 6).

AH1714/35624, and DPC6315/35624 were co-cultured at 100 ml scale, using the exact same cell numbers to inoculate all 100 ml cultures. OD-Standardized inoculums were added to 100 ml Allergen Free Medium, 4.5% Sucrose, 0.05% Cysteine which was used for all strains. The incubation of strains only vs. strains in combination was done at 37° C. for 24 hours. The results of this experiment gave us a better indication of the co-culturing capabilities of these strains. Rifampicin resistant variants of 35624 were used to allow detection of the strain on harvest. This variation consists of a point mutation in the rifampicin antibiotic resistance gene. 35624 was cultivated and viable counting on rifampicin-containing agar medium was performed to get an accurate cell count of 35624 in the culture experiments.

| Individual strain | Individual strain | Combination |
|---|---|---|
| Control (2% 35624-Rif) | Control (2% AH1714) | AH1714/35624-Rif (2% each) |
| Control (2% 35624-Rif) | Control (2% DPC6315) | DPC6315/35624-Rif (2% each) |

Figure 18A:
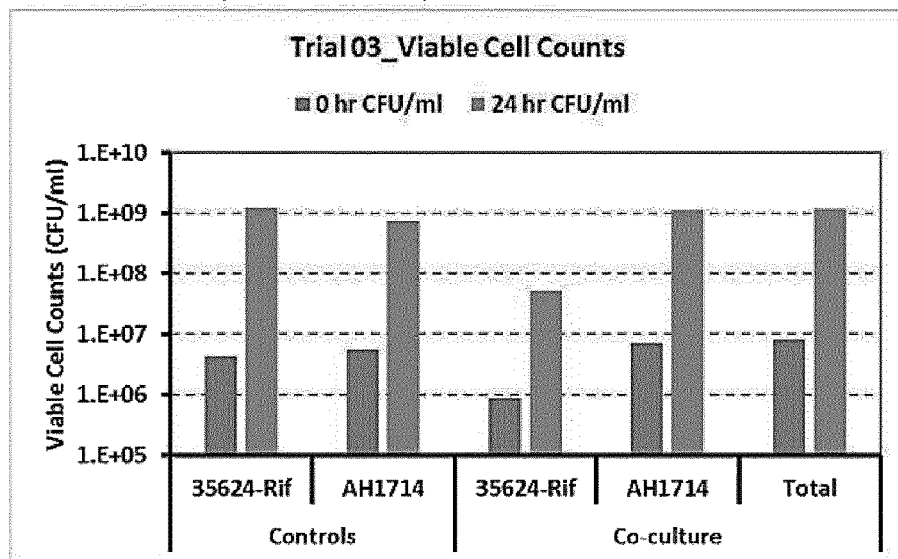
FIGS. 18(a) and (b) are charts of overnight cultures of 35624 either alone or in combination with 1714, or DPC6315.

AH1714/35624 co-culturing experiment: there was no major inhibition of either strain and the CFU/ml or growth for each was similar to the growth in the co-culture to both strains together (7.9e8 CFU/ml 35624 rif and 7.2e8 CFU/ml AH1714) (FIG. 18(a)).

Figure 18B:
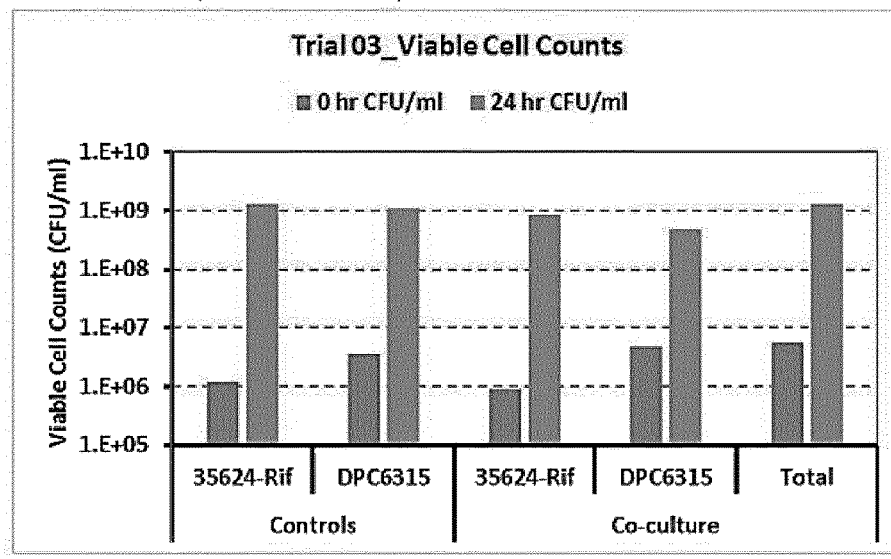

DPC6315/35624 co-culturing experiment: there was no major inhibition of either strain and the CFU/ml for each was similar as in the co-culture of both strains together (9.4e8 CFU/ml 35624 rif and 8.5e8 CFU/ml AH1714) (FIG. 18(b)).

This result showed that there was no detrimental interaction between 35624 and 1714.

Example 6

Anti-Inflammatory (IL-10/IL-12 ratios) PBMC Profiles of 35624, AH1714 and DPC6315

We had previously demonstrated that B. longum 35624 has an anti-inflammatory profile in vitro and that this type of profile may have relevance in IBS. Therefore, the aim of this study was to determine if we could find similar anti-inflammatory Bifidobacteria longum strains which we could partner with B. longum 35624 to make an enhanced anti-inflammatory combination. We screened 15 different B. longum including both B. longum DPC6315 and B. longum 1714 for their anti-inflammatory strain profile. To determine this, we measure both IL-10 and IL-12 from PBMCs stimulated in vitro with these bacterial strains.

Interleukin-10 (IL-10) is an anti-inflammatory cytokine which is produced by many cell types including monocytes, macrophages, dendritic cells, mast cells and lymphocytes (T regulatory cells). IL-10 down-regulates the expression of pro-inflammatory Th1 cytokines, MHC class II antigens, and co-stimulatory molecules on antigen presenting cells. It also enhances B cell survival, proliferation, and antibody production. This cytokine can block NF-κB activity and is involved in the regulation of the JAK-STAT signalling pathway. Murine knock-out studies have demonstrated the essential role for IL-10 in immunoregulation as IL-10KO mice develop severe colitis. In addition, bacteria which are potent inducers of IL-10 have been shown to promote T regulatory cell differentiation in vivo thus contributing to immunological homeostasis (O'Mahony et al., AJP 2006; O'Mahony et al., PLoS Pathogens 2008).

Interleukin-12 (IL-12) is a pro-inflammatory cytokine associated with polarisation of Th1 effector T cell responses and stimulates the production of other pro-inflammatory Th1 cytokines, such as interferon-gamma (IFN-γ) and tumour necrosis factor-alpha (TNF-α), from T and natural killer (NK) cells. High levels of IL-12 expression is associated with autoimmunity. Administration of IL-12 to people suffering from autoimmune diseases was shown to worsen disease symptoms. In contrast, IL-12 knock-out mice or treatment of mice with IL-12 neutralising antibodies ameliorated the disease.

Cytokine cascades and networks control the inflammatory response, rather than the action of a cytokine on a cell type. The relative levels of expression, or balance, of two cytokines (such as IL-10 and IL-12) is more informative than the expression of a single cytokine. In these studies, we stimulated human PBMCs with a range of different bacterial strains. All strains induced IL-10 and all strains induced IL-12. However, examination of the ratio between IL-10 and IL-12 induction revealed that some bacterial strains induced a higher ratio (i.e. more IL-10 with less IL-12) compared to other strains. This is a meaningful observation as it is the balance between each of these opposing signals that ultimately determines the immunological outcome. It is anticipated that a high IL-10:IL-12 ratio would promote an anti-inflammatory response associated with appropriate immunoregulatory activity while a low IL-10:IL-12 ratio would contribute to Th1 polarisation of the immune response. Thus, the PBMC IL-10:IL-12 ratio is an important selection criterion for identification of bacterial strains with immunoregulatory properties.

The assay was performed as described below:

Peripheral blood mononuclear cells (PBMCs) were isolated from fresh healthy human peripheral blood using BD Vacutainer CPT tubes (BD catalog 362761), as per the manufacturer's instructions. PBMCs were washed and resuspended in Dulbecco's Modified Eagle Medium-Glutamax™ (Glutamax (Glutamine substitute)+pyruvate+4.5 g/l glucose (Gibco catalog 10569-010) 10% fetal bovine serum (Sigma catalog F4135), and 1% penicillin/streptomycin (Sigma catalog P0781). Add 200 µL, of PBMC at a concentration of $1\times10^6$ cells/mL (i.e. $2\times10^5$ cells) to a flat-bottomed 96-well plate and add 20 µL of bacteria (at a concentration of $1\times10^7$ CFU/mL) to the required wells i.e. 20 µL stimulant/200 mL cells. Incubate the plates as required at 37° C./5% CO2 in an incubator.

The bacteria were generated as follows: For fresh broths bacteria were grown in Difco MRS media and harvested just after entering stationary phase. All cells were grown under anaerobic conditions at 37° C. For freeze dried products bacteria were grown in Difco MRS Media and harvested just after entering stationary phase. Cells were grown under anaerobic conditions at 37° C. The freeze-dried powders were then generated for each of these bacteria and stored by us at −80 C in pre-aliquoted 100 mg vials until just before use. Once they were removed from the freezer, a single vial was thawed to room temperature and washed 3 times in 10 ml ringers followed by centrifugation. A fresh vial was used on each occasion. Total bacterial counts were formed as described below. The lyophilised bacterial aliquoted into sterile tubes should be diluted in 10 ml of culture media (RPMI or DMEM). Take 1 ml from this tube and add to 4.5 ml of culture media (RPMI or DMEM) this will be the top dose at a concentration of 1.0E+09 then this will be diluted either 1:1 (medium dose) or 1:9 for the (lower dose). Add either 20 µL of the bacterial solution to 200 µl of PBMC suspensions ($2\times10^5$ cells) or 50 µl of the bacterial solution 500 µl PBMC suspensions ($5\times10^5$ cells) or 100 µl. The usual dilution selected was 1.0E+08, corresponding to 100:1 (bacteria:PBMC). The negative control is just the cryoprotectant which should be added to the unstimulated cells, but it should be diluted the same way as the bacterial aliquots. All assays were done in triplicate. After a 1-day incubation at 37° C., the plates were spun at 300×g, and the supernatants were removed and stored frozen at −80° C. until analysis. Cytokines in the culture supernatants were assayed using a 96-well assay kit from Meso Scale Discovery (Gaithersburg, Md.; catalog K15008B-1), Interleukin 10 (Il-10), and Interleukin 12p70 (Il12p70), and were quantitated and reported as picograms per millilitre. Each sample was assayed in duplicate. FIGS. show the results of a representative experiment.

Figure 19:
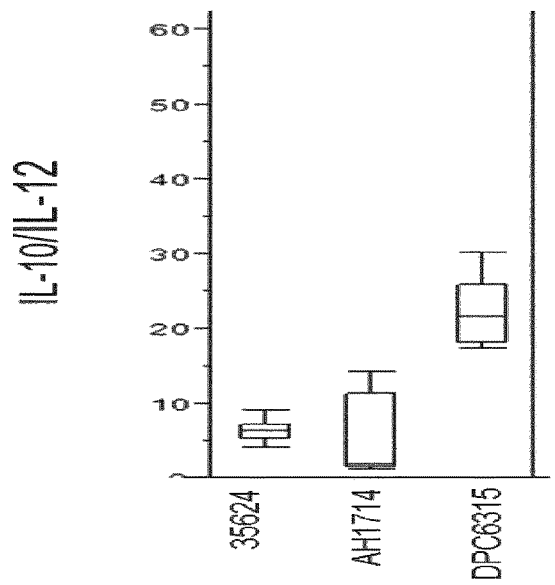
FIG. 19 is a plot of IL-10/IL-12 ratios from PBMC stimulated with Bif35624, AH1714 and DPC6315 in vitro.

Of the 15 strains tested, three bifidobacterial longum strains assayed, *B. longum* 35624 and *B. longum* 1714 induce a very similar and desired IL-10/IL-12 ratio. *B. longum* DPC6315 gave a higher ratio than either 35624 or 1714 which was similarly a desirable trait (FIG. 19).

Figure 20:
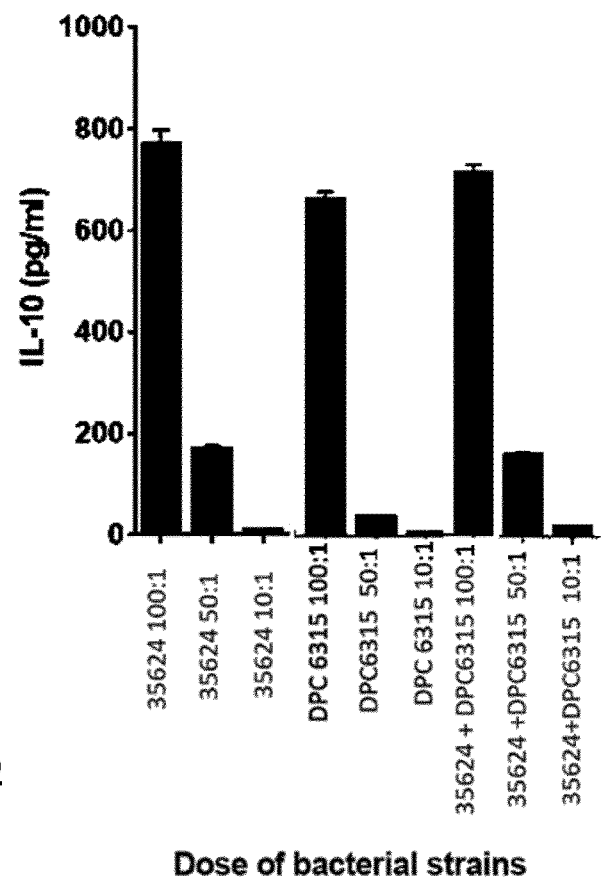
FIG. 20 is a bar chart of IL-10 levels from PBMC stimulated with Bif35624, or DPC6315 or a combination of both in vitro.

In addition, and to try to determine if there were negative effects of combining the strains we assessed IL-10 production of PBMCs stimulated with 35624 and DPC6315 and as a combination of the 2 strains. No negative effects of using both strains in combination in vitro were observed and similar IL-10 production were achieved as the strains used singly (FIG. 20). A similar result is obtained when 35624 is used in combination with 1714. Therefore, it was our hypothesis from all the available information in the literature and from these results that *B. longum* DPC6315 combined with *B. longum* 35624 should also be a great combinatory anti-inflammatory product.

Example 7

Strain Comparison in an Anti-Inflammatory Collagen-Induced Arthritis (CIA) model To further test the 35624/DPC6315 combination the strains were combined in a mouse model of inflammation. We have previously demonstrated that consumption of specific probiotic bacterial strains can modulate mucosal inflammatory disease. The aim of this study was to determine the effect of oral administration of probiotic *bifidobacteria longum* strains in a murine arthritis model either used singly or in combination in a well-established anti-inflammatory strain screening model. IBS is associated with higher levels of inflammation. Mouse models for IBS that assess anti-inflammatory effects are not well established therefore a well validated anti-inflammatory model was used. These novel *bifidobacteria* strains were identified to have anti-inflammatory profiles in vitro.

From our PBMC screen (example 5) we choose *B. longum* DPC6315, to determine if the known probiotic *B. longum* 35624 therapeutic effect was able to be enhanced when used in together with the anti-inflammatory *B. longum* DPC6315. These strains did not inhibit the growth of each other in co-culture experiments.

Mice were orally fed *B. longum* 35624, *B. longum* DPC6315 or a combination of both. Arthritis onset and disease severity in the CIA model of arthritis were the main parameters measured using the endpoints such as clinical signs of disease and paw swelling.

Rheumatoid arthritis (RA) is a chronic autoimmune disease affecting 1-2% of the Caucasian population. RA is characterized by inflammation of the joint synovial membrane, cartilage degradation and bone erosion. Joint damage occurs early during RA and once present is largely irreversible. Dysregulated expression of pro-inflammatory cytokines TNF, IL-6 and IFN-γ and anti-inflammatory IL-10 have been reported (Fieldman et al., 1996, Annu Rev Immunol 14; 397-440) as have high levels of IL-15 (McInnes I B et al., Nat Med 1996, 2:175-182) and IL-17 (McInnes I B et al., Arthritis Res 2000, 2:374-378). The relevance of TNF-α and IL-1β to disease pathogenesis has been highlighted by the clinical success of therapeutic strategies neutralizing TNFα or IL-1β Elliott M J et al., Lancet 1994, 344:1105-1110. Moreland L W et al., N Engl J Med 1997, 337:141-147. Feldmann M: Nat Rev Immunol 2002, 2:364-3711. Collagen-induced arthritis is a well-known Murine model of human RA and has may characteristics of both humoral and cellular immune mechanisms like those found in RA (Durie F H et al., Clin Immunol Immunopathol 1994; 73:11-18). The inflammatory infiltrate in mice and rats with type II collagen arthritis consists of neutrophils and macrophages with smaller numbers of lymphocytes when the lesions are in the acute to subacute phase. Tissue edema and neutrophil exudates within the joint space are common in the acute to subacute phase. As the inflammation progresses to chronic, mononuclear inflammatory cells (monocytes, lymphocytes) predominate and fibroblast proliferation, often with deposition of metachromatic matrix, occurs in synovium and periarticular tissue. Exudate is less common in the joint space.

Unless indicated in the comments area, the inflammation type is acute to subacute.

The assay was performed as described below.

Experimental Design

Animals (15 DBA/1 mice/group for arthritis) were anaesthetized with Isoflurane, shaved at the base of the tail, and injected intradermally with 150 µl of Freund's Complete Adjuvant (Difco) containing bovine type II collagen (Bolder BioPATH, Batch #5) (1 mg/ml) at the base of the tail on day 0 and again on day 21. On study day −14, mice were randomized by body weight into treatment groups. Treatment was initiated after enrolment and continued daily (QD at 24 h intervals) as indicated through study day 34 (treatment with positive control Dexamethasone was initiated on d18). On study days 24-35, onset of arthritis occurred. Mice were terminated on study day 35. Clinical scores were given for each of the paws (right front, left front, right rear, left rear) on days 18-35.

Observations, Measurements, and Specimens

Once disease is induced mice are observed for clinical signs of disease. Daily clinical scores were given for each of the paws (right front, left front, right rear, left rear) on study days 18-35 using the following criteria:
0=Normal.
1=One hind or fore paw joint affected or minimal diffuse erythema and swelling.
2=Two hind or fore paw joints affected or mild diffuse erythema and swelling.
3=Three hind or fore paw joints affected or moderate diffuse erythema and swelling.
4=Four hind or fore paw joints affected or marked diffuse erythema and swelling.
5=Entire paw affected, severe diffuse erythema and severe swelling, unable to flex Inflammation Scoring
0=Normal.
0.5=Very minimal, affects only 1 joint or minimal multifocal periarticular infiltration of inflammatory cells.
1=Minimal infiltration of inflammatory cells in synovium and periarticular tissue of affected joints.
2=Mild infiltration of inflammatory cells. If referring to paws, generally restricted to affected joints (1-3 affected).
3=Moderate infiltration with moderate edema. If referring to paws, restricted to affected joints, generally 3-4 joints and the wrist or ankle.
4=Marked infiltration affecting most areas with marked edema, 1 or 2 unaffected joints may be present.
5=Severe diffuse infiltration with severe edema affecting all joints (to some extent) and periarticular tissues.

Clinical data for paw scores (means for animal) were analysed by determining the area under the dosing curve (AUC) for days 18-35. For calculation of AUC, the daily mean scores for each mouse was entered Microsoft Excel and the area between the treatment days and the final day was computed. Means for each group were determined and % inhibition from arthritis controls were calculated by comparing values for treated and normal animals. Data were analysed using a one-way analysis of variance (1-way ANOVA) or Kruskal-Wallis test (non-parametric), along with the appropriate multiple comparison post-test. The model was validated by comparing normal controls to disease controls using a Student's two-tailed t-test. Statistical tests make certain assumptions regarding the data's normality and homogeneity of variance, and further analysis may be required if testing resulted in violations of these assumptions. Significance for all tests was set at p<0.05.

Figure 21:
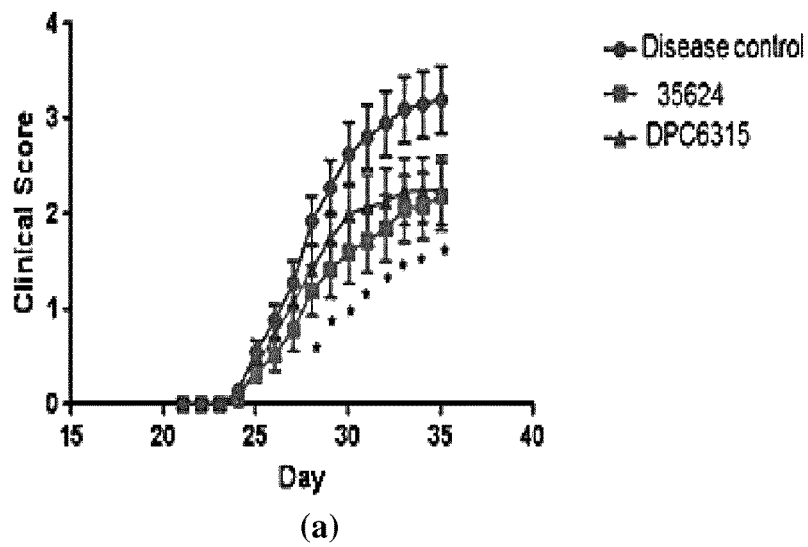
FIGS. 21(a) and (b) are graphs of Clinical Arthritis Score-All paws (Score 0-5) after feeding with Bif35624, DPC6315 or a combination of both.
Figure 21:
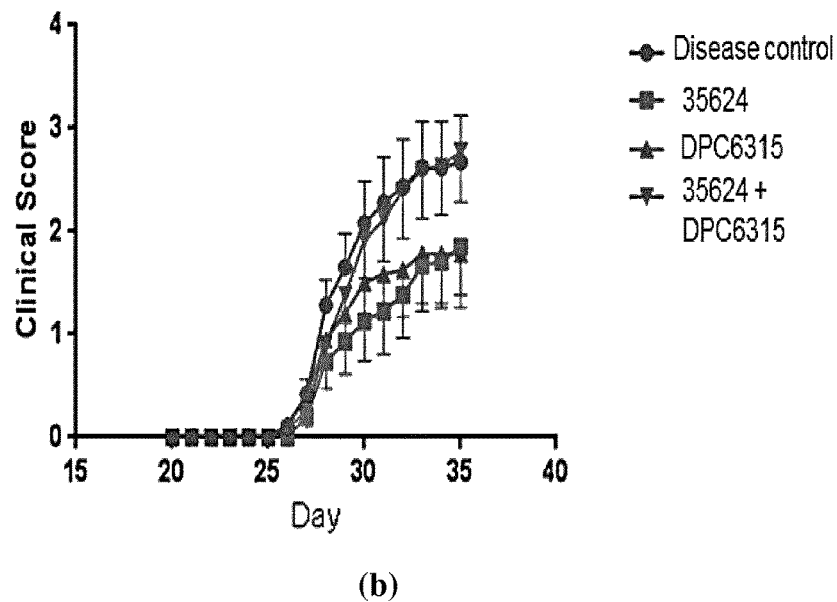
Figure 22:
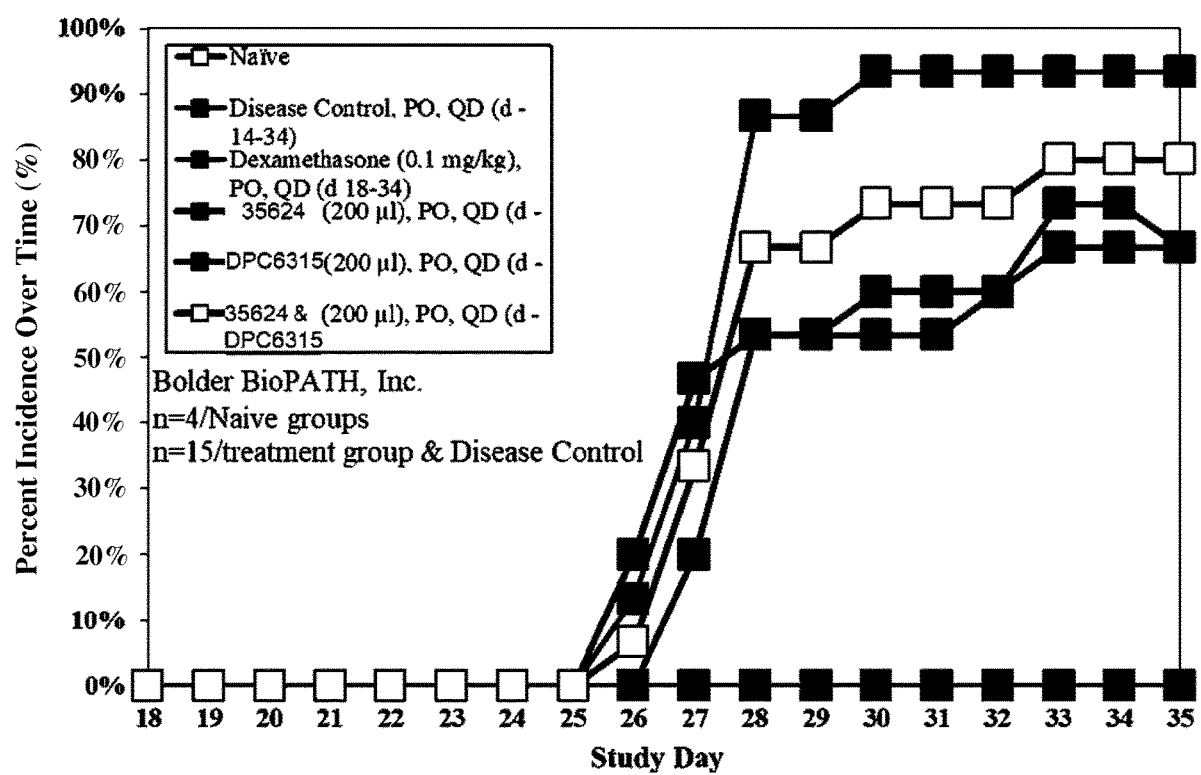
FIG. 22 is a plot of percent incidence over time after feeding with Bif35624, DPC6315 or a combination of both.

B. longum 35624 feeding resulted in reduced inflammation and clinical signs of disease compared to the disease control group (*p<0.05) (FIG. 21(a)) or the combination of DPC6315 and 35624 feeding group (FIG. 21(b)). In agreement with this, B. longum 35624 consumption delayed disease onset and severity as measured by percent incidence of disease while the combination of the two Bifidobacteria longum or DPC6315 alone did not, although DPC 6315 displayed a similar trend to 35624 (FIG. 22). In conclusion an oral administration of the probiotic B. longum 35624 was demonstrably better than the combined product for reduced inflammation via joint scores, and incidence and resulted in significant improvement in the visual assessment of arthritis in the collagen-induced arthritis model. This was an unexpected result as these were the best two candidate strains from the in-vitro PBMC tests and where there was no inhibition of growth in the co-culturing experiments. B. longum DPC6315 inhibited the anti-inflammatory effect of 35624 in a mouse model of arthritis (CIA) when combined and the combination was worse than either strain alone. This study demonstrates that the effect of combinations of Bifidobaceterium longum strains can be unpredictable in vivo.

The strains of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound. In addition, a vaccine comprising the strains of the invention may be prepared using any suitable known method and may include a pharmaceutically acceptable carrier or adjuvant.

The introduction of probiotic organisms is accomplished by the ingestion of the micro-organism in a suitable carrier. It would be advantageous to provide a medium that would promote the growth of these probiotic strains in the large bowel. The addition of one or more oligosaccharides, polysaccharides, or other prebiotics enhances the growth of lactic acid bacteria in the gastrointestinal tract. Prebiotics refers to any non-viable food component that is specifically fermented in the colon by indigenous bacteria thought to be of positive value, e.g. bifidobacteria, lactobacilli. Types of prebiotics may include those that contain fructose, xylose, soya, galactose, glucose and mannose. The combined administration of a probiotic strain with one or more prebiotic compounds may enhance the growth of the administered probiotic in vivo resulting in a more pronounced health benefit and is termed synbiotic.

It will be appreciated that the probiotic strains may be administered prophylactically or as a method of treatment either on their own or with other probiotic and/or prebiotic materials as described above. In addition, the bacteria may be used as part of a prophylactic or treatment regime using other active materials such as those used for treating inflammation or other disorders especially those with an immunological involvement. Such combinations may be administered in a single formulation or as separate formulations administered at the same or different times and using the same or different routes of administration.

The strains of the invention may be formulated to facilitate controlled release such as a delayed release of the strain. For example, the formulation may be adapted to release the strain at a particular location in the gastrointestinal tract such as the small intestine or in the colon. To achieve such a controlled release the strain may be formulated in a capsule which has a coating which is adapted to release the strain at a particular location. A range of coatings are available to facilitate such controlled release. One such family of coatings are those available under the Trade Mark Eudragit.

The invention is not limited to the embodiments hereinbefore described, which may be varied in detail.

REFERENCES

ALLEN, A. P., HUTCH, W., BORRE, Y. E., KENNEDY, P. J., TEMKO, A., BOYLAN, G., MURPHY, E., CRYAN, J. F., DINAN, T. G. & CLARKE, G. 2016. *Bifidobaceterium longum* 1714 as a translational psychobiotic: modulation of stress, electrophysiology and neurocognition in healthy volunteers. *Transl Psychiatry*, 6, e939.

ANDERSSON, H., TULLBERG, C., AHRNE, S., HAMBERG, K., LAZOU AHREN, I., MOLIN, G., SONESSON, M. & HAKANSSON, A. 2016. Oral Administration of *Lactobacillus plantarum* 299v Reduces Cortisol Levels in Human Saliva during Examination Induced Stress: A Randomized, Double-Blind Controlled Trial. *Int J Microbiol*, 2016, 8469018.

BLANCHARD, E. B., LACKNER, J. M., JACCARD, J., ROWELL, D., CAROSELLA, A. M., POWELL, C., SANDERS, K., KRASNER, S. & KUHN, E. 2008. The role of stress in symptom exacerbation among IBS patients. *J Psychosom Res*, 64, 119-28.

BUYSSE DJ, REYNOLDS CF, MONK TH, BERMAN SR, KUPFER DJ 1989 The Pittsburgh Sleep Quality Index: a new instrument for psychiatric practice and research. Psychiatry Res. May; 28(2): 193-213.

BUYSSE DJ, REYNOLDS CF 3RD, MONK TH, HOCH CC, YEAGER A L, KUPFER DJ. 1991 Quantification of subjective sleep quality in healthy elderly men and women using the Pittsburgh Sleep Quality Index (PSQI) Sleep. August; 14(4):331-8.

CHITKARA, D. K., VAN TILBURG, M. A., BLOIS-MARTIN, N. & WHITEHEAD, W. E. 2008. Early life risk factors that contribute to irritable bowel syndrome in adults: a systematic review. *Am J Gastroenterol*, 103, 765-74; quiz 775.

CHOGHAKHORI CHOGHAKHORI R, ABBASNEZHAD A, HASANVAND A, AMANI R. 2017 Inflammatory cytokines and oxidative stress biomarkers in irritable bowel syndrome: association with digestive symptoms and quality of life. Cytokine; 93:34-43.

DINAN, T. G. & CRYAN, J. F. 2017. The Microbiome-Gut-Brain Axis in Health and Disease. *Gastroenterol Clin North Am*, 46, 77-89.

DROSSMAN, D. A. & HASLER, W. L. 2016. Rome IV-Functional GI Disorders: Disorders of Gut-Brain Interaction. *Gastroenterology*, 150, 1257-61.

EFSA BIOHAZ PANEL (EFSA PANEL ON BIOLOGICAL HAZARDS. 2013. Scientific Opinion on the maintenance of the list of QPS biological agents intentionally added to food and feed (2013 update). EFSA Journal, 11 3449.

ELLIOTT M J, MAINI R N, FELDMANN M, KALDEN J R, ANTONI C, SMOLEN J S, LEEB B, BREEDVELD F C, MACFARLANE J D, BIJL H, et al. Randomised double-blind comparison of chimeric monoclonal antibody to tumour necrosis factor alpha (cA2) versus placebo in rheumatoid arthritis. Lancet. 1994 Oct. 22; 344 (8930):1105-10.

ENCK P, AZIZ Q, BARBARA G, FARMER A D, FUKUDO S, MAYER EA, NIESLER B, QUIGLEY E M, RAJILIĆSTOJANOVIĆ M, SCHEMANN M, SCHWILLE-KIUNTKE J, SIMREN M, ZIPFEL S, SPILLER R C. Irritable bowel syndrome. Nat Rev Dis Primers. 2016 Mar. 24; 2:16014.

FELDMANN M, BRENNAN F M, MAINI R N. Role of cytokines in rheumatoid arthritis. Annu Rev Immunol. 1996; 14:397-440.

FELDMANN M. Development of anti-TNF therapy for rheumatoid arthritis. Nat Rev Immunol. 2002 May; 2(5): 364-71.

FILLINGIM R B, OHRBACH R, GREENSPAN J D, KNOTT C, DUBNER R, BAIR E, BARAIAN C, SLADE G D, MAIXNER W. 2011 Potential psychosocial risk factors for chronic TMD: descriptive data and empirically identified domains from the OPPERA patient-control study. J Pain.; 12:T46-T60.

FORD, A. C., QUIGLEY, E. M., LACY, B. E., LEMBO, A. J., SAITO, Y. A. & SCHILLER, L. R. 2014. Efficacy of prebiotics, probiotics, and synbiotics in irritable bowel syndrome and chronic idiopathic constipation: Systematic review and meta-analysis. *Am J Gastroenterol*, 109.

FRANCIS C. Y., MORRIS J., WHORWELL P. J. 1997 The irritable bowel severity scoring system: a simple method of monitoring irritable bowel syndrome and its progress. Aliment Pharmacol Ther. April; 11(2):395-402.

GROEGER, D., O'MAHONY, L., MURPHY, E. F., BOURKE, J. F., DINAN, T. G., KIELY, B., SHANAHAN, F. & QUIGLEY, E. M. 2013. *Bifidobaceterium infantis* 35624 modulates host inflammatory processes beyond the gut. *Gut Microbes*, 4, 325-39.

HERMAN C R, SCHIFFMAN E L, LOOK J O, RINDAL D B 2002 The effectiveness of adding pharmacologic treatment with clonazepam or cyclobenzaprine to patient education and self-care for the treatment of jaw pain upon awakening: a randomized clinical trial. J Orofac Pain.; 16:64-70.

HUNGIN, A. P., WHORWELL, P. J., TACK, J. & MEARIN, F. 2003. The prevalence, patterns and impact of irritable bowel syndrome: an international survey of 40,000 subjects. *Aliment Pharmacol Ther,* 17, 643-50.

JEFFERY, I. B., O'TOOLE, P. W., OHMAN, L., CLAESSON, M. J., DEANE, J., QUIGLEY, E. M. & SIMREN, M. 2012. An irritable bowel syndrome subtype defined by species-specific alterations in faecal microbiota. *Gut*, 61, 997-1006.

KELL, D. B., KAPRELYANTS A. S., WEICHART D. H., HARWOOD C. R., BARER M. R. 1998 Viability and activity in readily culturable bacteria: a review and discussion of the practical issues. Antonie Van Leeuwenhoek February; 73(2):169-87.

KENNEDY, P. J., CLARKE, G., O'NEILL, A., GROEGER, J. A., QUIGLEY, E. M., SHANAHAN, F., CRYAN, J. F. & DINAN, T. G. 2014. Cognitive performance in irritable bowel syndrome: evidence of a stress-related impairment in visuospatial memory. *Psychol Med*, 44, 1553-66.

KONIECZNA, P., GROEGER, D., ZIEGLER, M., FREI, R., FERSTL, R., SHANAHAN, F., QUIGLEY, E. M., KIELY, B., AKDIS, C. A. & O'MAHONY, L. 2012. *Bifidobacterium infantis* 35624 administration induces Foxp3 T regulatory cells in human peripheral blood: potential role for myeloid and plasmacytoid dendritic cells. *Gut*, 61, 354-66.

LI, T., YU, T., HAWKINS, B. S. & DICKERSIN, K. 2015. Design, Analysis, and Reporting of Crossover Trials for Inclusion in a Meta-Analysis. *PLoS ONE*, 10, e0133023.

MESSAOUDI, M., LALONDE, R., VIOLLE, N., JAVELOT, H., DESOR, D., NEJDI, A., BISSON, J. F., ROUGEOT, C., PICHELIN, M., CAZAUBIEL, M. & CAZAUBIEL, J. M. 2011a. Assessment of psychotropic-like properties of a probiotic formulation (*Lactobacillus helveticus* R0052 and *Bifidobaceterium longum* R0175) in rats and human subjects. *Br J Nutr,* 105, 755-64.

MESSAOUDI, M., VIOLLE, N., BISSON, J. F., DESOR, D., JAVELOT, H. & ROUGEOT, C. 2011B. Beneficial psychological effects of a probiotic formulation (*Lactobacillus helveticus* R0052 and *Bifidobaceterium longum* R0175) in healthy human volunteers. *Gut Microbes*, 2, 256-61.

MIYAZAKI, K., ITOH, N., YAMAMOTO, S., HIGO-YAMAMOTO, S., NAKAKITA, Y., KANEDA, H., OISHI, K. (2014). Dietary heat-killed *Lactobacillus brevis* SBC8803 promotes voluntary wheel-running and affects sleep rhythms in mice. Life Sci, 111(1-2), 47-52.

MCINNES I. B., AL-MUGHALES J, FIELD M, LEUNG B P, HUANG F P, DIXON R, STURROCK R D, WILKINSON P C, LIEW F Y. Nat Med. 1996 February; 2(2):175-82. The role of interleukin-15 in T-cell migration and activation in rheumatoid arthritis.

MCINNES, I. B., LEUNG, B. P. and LIEW, F. Y. 2000. Cell-cell interactions in synovitis. Interactions between T lymphocytes and synovial cells, Arthritis Res. 2, 374-378.

MORELAND L W, BAUMGARTNER S W, SCHIFF M H, TINDALL EA, FLEISCHMANN R M, WEAVER A L, ETTLINGER R E, COHEN S, KOOPMAN W J, MOHLER K, WIDMER M B, BLOSCH C M. Treatment of rheumatoid arthritis with a recombinant human tumor necrosis factor receptor (p75)-Fc fusion protein. N Engl J Med. 1997 Jul. 17; 337(3):141-7.9

O'MAHONY, L., MCCARTHY, J., KELLY, P., HURLEY, G., LUO, F., CHEN, K., O'SULLIVAN, G. C., KIELY, B., COLLINS, J. K., SHANAHAN, F. & QUIGLEY, E. M. 2005. *Lactobacillus* and *bifidobacterium* in irritable bowel syndrome: symptom responses and relationship to cytokine profiles. *Gastroenterology*, 128, 541-51.

O'MAHONY L., O'CALLAGHAN L., MCCARTHY J., SHILLING D., SCULLY P., SIBARTIE S., KAVANAGH E., KIRWAN W. O., REDMOND H. P., COLLINS J. K., SHANAHAN F. Differential cytokine response from dendritic cells to commensal and pathogenic bacteria in different lymphoid compartments in humans. Am J Physiol Gastrointest Liver Physiol. 2006 April; 290(4): G839-45. Epub 2005 Nov. 17

O'MAHONY C., SCULLY P., O'MAHONY D., MURPHY S., O'BRIEN F., LYONS A., SHERLOCK G., MACSHARRY J., KIELY B., SHANAHAN F., O'MAHONY L. 2008 Commensal-induced regulatory T cells mediate protection against pathogen-stimulated NF-kappaB activation. PLoS Pathog. August 1; 4(8): e1000112.

O'MALLEY, D. 2015. Immunomodulation of enteric neural function in irritable bowel syndrome. *World J Gastroenterol*, 21, 7362-6.

FOOD AND AGRICULTURAL ORGANIZATION OF THE UNITED NATIONS AND WORLD HEALTH ORGANIZATION. 2001. Health and nutritional properties of probiotics in food including powder milk with live lactic acid bacteria. *World Health Organization [online]*. http://www.who.int/foodsafety/publications/fs_management/en/probiotics.pdf PINTO-SANCHEZ, M. I., HALL, G. B., GHAJAR, K., NARDELLI, A., BOLINO, C., LAU, J. T., MARTIN, F. P., COMINETTI, O., WELSH, C., RIEDER, A., TRAYNOR, J., GREGORY, C., DE PALMA, G., PIGRAU, M., FORD, A. C., MACRI, J., BERNER, B., BERGONZELLI, G., SURETTE, M. G., COLLINS, S. M., MOAYYEDI, P. & BERCIK, P. 2017. Probiotic *Bifidobaceterium longum* NCC3001 Reduces Depression Scores and Alters Brain Activity: a Pilot Study in Patients With Irritable Bowel Syndrome. *Gastroenterology*.

PORTO F, DE LEEUW R, EVANS D R, CARLSON C R, YEPES J F, BRANSCUM A, OKESON J P. 2011 Differences in psychosocial functioning and sleep quality between idiopathic continuous orofacial neuropathic pain patients and chronic masticatory muscle pain patients. J Orofac Pain.; 25:117-124

RANA S V, SHARMA S, SINHA S K, PARSAD K K, MALIK A, SINGH K. Pro-inflammatory and anti-inflammatory cytokine response in diarrhoea-predominant irritable bowel syndrome patients. Trop Gastroenterol 2012; 33:251-256.

SAVIGNAC, H. M., KIELY, B., DINAN, T. G. & CRYAN, J. F. 2014. Bifidobacteria exert strain-specific effects on stress-related behavior and physiology in BALB/c mice. *Neurogastroenterol Motil*, 26, 1615-27.

SAVIGNAC, H. M., TRAMULLAS, M., KIELY, B., DINAN, T. G. & CRYAN, J. F. 2015. Bifidobacteria modulate cognitive processes in an anxious mouse strain. *Behav Brain Res*, 287, 59-72.

SEYEDMIRZAEE S, HAYATBAKHSH M M, AHMADI B, ET AL. Serum immune biomarkers in irritable bowel syndrome. Clin Res Hepatol Gastroenterol 2016; 40:631-637117

SCHMULSON M, PULIDO-LONDON D, RODRIGUEZ O., ET AL. Lower serum IL-10 is an independent predictor of IBS among volunteers in Mexico. Am J Gastroenterol 2012; 107:747-753)

SUAREZ-HITZ K. A., OTTO B., BIDLINGMAIER M., SCHWIZER W., FRIED M., EHLERT U. 2012 Altered psychobiological responsiveness in women with irritable bowel syndrome. Psychosom Med. February-March; 74(2):221-31. 2012 Jan. 27.

TAP, J., DERRIEN, M., TORNBLOM, H., BRAZEILLES, R., COOLS-PORTIER, S., DORE, J., STORSRUD, S., LE NEVE, B., OHMAN, L. & SIMREN, M. 2017. Identification of an Intestinal Microbiota Signature Associated With Severity of Irritable Bowel Syndrome. *Gastroenterology*, 152, 111-123.e8.

TURRONI, F., PEANO, C., PASS, D. A., FORONI, E., SEVERGNINI, M., CLAESSON, M. J., KERR, C., HOURIHANE, J., MURRAY, D., FULIGNI, F., GUEIMONDE, M., MARGOLLES, A., DE BELLIS, G., O'TOOLE, P. W., VAN SINDEREN, D., MARCHESI, J. R. & VENTURA, M. 2012. Diversity of bifidobacteria within the infant gut microbiota. *PLoS One*, 7, e36957.

WHORWELL, P. J., ALTRINGER, L., MOREL, J., BOND, Y., CHARBONNEAU, D., O'MAHONY, L., KIELY, B., SHANAHAN, F. & QUIGLEY, E. M. 2006. Efficacy of an encapsulated probiotic *Bifidobaceterium* infantis 35624 in women with irritable bowel syndrome. *Am J Gastroenterol*, 101, 1581-90.

YAMAMURA, S., MORISHIMA, H., KUMANO-GO, T., SUGANUMA, N., MATSUMOTO, H., ADACHI, H., TAKEDA, M. (2007). The effect of *Lactobacillus helveticus* fermented milk on sleep and health perception in elderly subjects. Eur J Clin Nutr, 63(1), 100-105.

ZHEN Y, CHU C, ZHOU S, ET AL. Imbalance of tumor necrosis factor-alpha, interleukin-8 and interleukin-10 production evokes barrier dysfunction, severe abdominal symptoms and psychological disorders in patients with irritable bowel syndrome-associated diarrhoea. Mol Med Rep 2015; 12:5239-5245).

The invention claimed is:

1. A method of treating a human subject, the method comprising administering to the subject a formulation comprising a *Bifidobacterium* strain having accession number NCIMB 41003, a *Bifidobacterium* strain having accession number NCIMB 41676, and an ingestible carrier, wherein the subject has irritable bowel syndrome (IBS) and the treatment improves gastrointestinal symptoms associated with IBS and one or more of the following:
   improves mood associated with IBS;
   reduces stress associated with IBS;
   reduces anxiety associated with IBS;
   improves sleep quality associated with IBS;
   treats depression associated with IBS; or
   normalises dysregulated cortisol awakening response associated with IBS.

2. The method as claimed in claim 1, wherein the treatment improves inflammation associated with IBS.

3. The method of claim 1, wherein at least one of the *Bifidobacterium* strains is in the form of viable cells.

4. The method of claim 1, wherein at least one of the *Bifidobacterium* strains is in the form of non-viable cells.

5. The method of claim 1, wherein each of the *Bifidobacterium* strain NCIMB 41003 and the *Bifidobacterium* strain NCIMB 41676 is present in the formulation in an amount of more than $10^6$ cfu.

6. The method of claim 1, wherein the subject has anxiety or depression.

7. The method of claim 1, wherein the formulation is in the form of a broth, a powder, capsule, or tablet.

8. The method of claim 1, wherein the ingestible carrier is a food product chosen from acidified milk, a yoghurt, a frozen food, a gum, a candy, a milk powder, a milk concentrate, a cheese spread, a nutritional composition, a nutritional supplement, a cereal bar, a dressing, or a beverage.

9. The method of claim 1, wherein the formulation further comprises at least one of a prebiotic material, a protein, or a peptide.

10. The method of claim 1, wherein the formulation further comprises a lipid, a carbohydrate, a vitamin, a mineral, a trace element, or a combination thereof.

11. The method of claim 1, wherein the formulation further comprises a drug entity or a biological compound.

12. A method of treating inflammation in the gastrointestinal system of a subject, the method comprising administering to the subject a formulation comprising a *Bifidobac-*

*terium* strain having accession number NCIMB 41003 and a *Bifidobacterium* strain having accession number NCIMB 41676.

13. The method of claim 12, wherein the formulation is in the form of a broth, a powder, a capsule, or a tablet.

14. The method of claim 12, wherein the treatment improves inflammation associated with IBS.

15. The method of claim 12, wherein each of the *Bifidobacterium* strain NCIMB 41003 and the second *Bifidobacterium* strain NCIMB 41676 is present in the formulation in an amount of more than $10^6$ cfu.

16. The method of claim 12, wherein the formulation further comprises a food product.

17. The method of claim 1, wherein the formulation provides a dose of $5 \times 10^8$ cfu to $1 \times 10^9$ cfu per day per strain.

18. The method of claim 1, wherein the formulation decreases TNF-α in the subject.

* * * * *

UNITED STATES PATENT AND TRADEMARK OFFICE
CERTIFICATE OF CORRECTION

PATENT NO. : 11,400,123 B2
APPLICATION NO. : 16/767846
DATED : August 2, 2022
INVENTOR(S) : Barry Kiely et al.

It is certified that error appears in the above-identified patent and that said Letters Patent is hereby corrected as shown below:

On the Title Page

In Item (56) under OTHER PUBLICATIONS, replace "Herman, F.R." with --Herman, C.R.--.

In the Claims

In Claim 15, Column 25, Line 9, replace "the second" with --the--.

Signed and Sealed this
Twenty-second Day of November, 2022

*Katherine Kelly Vidal*

Katherine Kelly Vidal
*Director of the United States Patent and Trademark Office*